United States Patent
Zarembinski et al.

(10) Patent No.: US 10,137,199 B2
(45) Date of Patent: Nov. 27, 2018

(54) THIOLATED HYALURONAN-BASED HYDROGELS CROSS-LINKED USING OXIDIZED GLUTATHIONE

(71) Applicant: BioTime, Inc., Alameda, CA (US)

(72) Inventors: Thomas Zarembinski, Castro Valley, CA (US); Isaac Erickson, Alameda, CA (US); Nathaniel Doty, Alameda, CA (US)

(73) Assignee: BioTime, Inc., Alameda, CA (US)

( * ) Notice: Subject to any disclaimer, the term of this patent is extended or adjusted under 35 U.S.C. 154(b) by 1 day.

(21) Appl. No.: 14/275,795

(22) Filed: May 12, 2014

(65) Prior Publication Data

US 2014/0341842 A1 Nov. 20, 2014

Related U.S. Application Data

(60) Provisional application No. 61/823,322, filed on May 14, 2013.

(51) Int. Cl.

| | |
|---|---|
| *A61K 38/00* | (2006.01) |
| *A61K 47/36* | (2006.01) |
| *A61K 38/19* | (2006.01) |
| *A61K 31/195* | (2006.01) |
| *C08B 37/08* | (2006.01) |
| *A61K 47/42* | (2017.01) |
| *A61K 9/06* | (2006.01) |
| *A61K 35/12* | (2015.01) |
| *A61K 45/00* | (2006.01) |

(52) U.S. Cl.
CPC ............... *A61K 47/36* (2013.01); *A61K 9/06* (2013.01); *A61K 31/195* (2013.01); *A61K 35/12* (2013.01); *A61K 38/193* (2013.01); *A61K 45/00* (2013.01); *A61K 47/42* (2013.01); *C08B 37/0072* (2013.01)

(58) Field of Classification Search
None
See application file for complete search history.

(56) References Cited

U.S. PATENT DOCUMENTS

| | | | |
|---|---|---|---|
| 7,928,069 B2 | 4/2011 | Prestwich et al. | |
| 7,981,871 B2 | 7/2011 | Prestwich et al. | |
| 2005/0181018 A1* | 8/2005 | Peyman | 424/427 |
| 2009/0117656 A1* | 5/2009 | Akashi | A61L 27/52 435/397 |

OTHER PUBLICATIONS

Lowe et al. Polym. Chem., 2010, 1, 17-36. DOI: 10.1039/b9py00216b.*
Burdick and Prestwich. Adv Mater. Mar. 25, 2011; 23(12): H41-H56. doi:10.1002/adma.201003963.*
Ballios, B.G. et al., "A hydrogel-based stem cell delivery system to treat retinal degenerative diseases," Biomaterials. 31(9), 2010, 2555-64.
Burdick, J.A. et al., "Controlled degradation and mechanical behavior of photopolymerized hyaluronic acid networks," Biomacromolecules. 6(1), 2005, 386-91.
Cai, S. et al., "Injectable glycosaminoglycan hydrogels for controlled release of human basic fibroblast growth factor," Biomaterials. 26(30), 2005, 6054-67.
Caicco, M.J. et al., "Characterization of hyaluronan-methylcellulose hydrogels for cell delivery to the injured spinal cord," J Biomed Mater Res A. 101(5), 2013, 1472-7.
Compte, M. et al., "Tumor immunotherapy using gene-modified human mesenchymal stem cells loaded into synthetic extracellular matrix scaffolds," Stem Cells. 27(3), 2009, 753-60.
Contreras-Ruiz, L. , "Intracellular trafficking of hyaluronic acid-chitosan oligomer-based nanoparticles in cultured human ocular surface cells," Mol Vis. 27; 17, 2011, 279-90.
Cooper, A.J. et al., "Reversible and irreversible protein glutathionylation: biological and clinical aspects," Expert Opin Drug Metab Toxicol. 7(7), 2011, 891-910.
Desai, V.D. et al., "CD44 expression is developmentally regulated in the mouse lens and increases in the lens epithelium after injury," Differentiation. 79(2), 2010, 111-9.
Du, Y. et al., "Adipose-derived stem cells differentiate to keratocytes in vitro," Mol Vis. 10;16, 2010, 2680-9.
Engler, A.J. et al., "Matrix elasticity directs stem cell lineage specification," Cell. 25; 126(4), 2006, 677-89.
Espandar, L. et al., "Adipose-derived stem cells on hyaluronic acid-derived scaffold: a new horizon in bioengineered cornea," Arch Ophthalmol. 130(2), 2012, 202-8.
Fairbanks, B.D. et al., "A Versatile Synthetic Extracellular Matrix Mimic via Thiol-Norbornene Photopolymerization," Adv Mater. 28; 21(48), 2009, 5005-10.
Forman, H.J. et al., "Glutathione: overview of its protective roles, measurement, and biosynthesis," Mol Aspects Med. 30(1-2), 2009, 1-12.
Gallogly, M.M. et al., "Mechanistic and kinetic details of catalysis of thiol-disulfide exchange by glutaredoxins and potential mechanisms of regulation," Antioxid Redox Signal. 11(5), 2009, 1059-81.
Gamini, A. et al., "Structural investigations of cross-linked hyaluronan," Biomaterials. 23(4), 2002, 1161-7.
Garbern, J.C. et al., "Delivery of basic fibroblast growth factor with a pH-responsive, injectable hydrogel to improve angiogenesis in infarcted myocardium," Biomaterials. 32(9), 2011, 2407-16.
Gaudana, R. et al., "Recent perspectives in ocular drug delivery," Pharm Res. 26(5), 2009, 1197-216.
Hanjaya-Putra, D. et al., "Vascular endothelial growth factor and substrate mechanics regulate in vitro tubulogenesis of endothelial progenitor cells," J Cell Mol Med. 14(10), 2010, 2436-47.
Keller, K.E. et al., "Inhibition of hyaluronan synthesis reduces versican and fibronectin levels in trabecular meshwork cells," PLoS One. 7(11), 2012, e48523.
Klein, E.A. et al., "Cell-cycle control by physiological matrix elasticity and in vivo tissue stiffening," Curr Biol. 29;19(18), 2009, 1511-8.
Kompella, U.B. et al., "Recent advances in ophthalmic drug delivery," Ther Deliv. 1(3), 2010, 435-56.

(Continued)

*Primary Examiner* — Jeanette M Lieb

(74) *Attorney, Agent, or Firm* — McCarter & English, LLP; Jonathan M. Sparks

(57) ABSTRACT

The invention provides methods, compositions and kits relating to hyaluronan based matrices using oxidized glutathione as a crosslinking agent.

31 Claims, 5 Drawing Sheets

(56) References Cited

OTHER PUBLICATIONS

Koutsopoulos, S. et al., "Controlled release of functional proteins through designer self-assembling peptide nanofiber hydrogel scaffold," Proc Natl Acad Sci U S A. 24;106(12), 2009, 4623-8.
Laflamme, M. et al., "Cardiomyocytes derived from human embryonic stem cells in pro-survival factors enhance function of infarcted rat hearts," Nature Biotechnol. 25, 2007, pp. 1015-1024.
Laurent, T.C. et al., "Hyaluronan," FASEB J. 6(7), 1992, 2397-404.
Lee, K.Y. et al., "Hydrogels for tissue engineering," Chem Rev. 101(7), 2001, 1869-79.
Liang, Y. et al., "Tuning the non-equilibrium state of a drug-encapsulated poly(ethylene glycol) hydrogel for stem and progenitor cell mobilization," Biomaterials. 32(7), 2011, 2004-12.
Liu, Y. et al., "The application of hyaluronic acid hydrogels to retinal progenitor cell transplantation," Tissue Eng Part A. 19(1-2), 2013, 135-42.
Mahnd-Kaci, F. et al., "Optimized hyaluronic acid-hydrogel design and culture conditions for preservation of mesenchymal stem cell properties," Tissue Eng Part C Methods. 19(4), 2013, 288-98.
Martínez-Conesa, E.M. et al., "Characterization of ocular surface epithelial and progenitor cell markers in human adipose stromal cells derived from lipoaspirates," Invest Ophthalmol Vis Sci. 31;53(1), 2012, 513-20.
Mazumder, M.A. et al., "Cell-adhesive thermogelling PNIPAAm/hyaluronic acid cell delivery hydrogels for potential application as minimally invasive retinal therapeutics," J Biomed Mater Res A. 100(7), 2012, 1877-87.
Meister, A., "Glutathione metabolism and its selective modification," J Biol Chem. 25;263(33), 1988, 17205-8.
Mooney, D.J. et al., "Cell delivery mechanisms for tissue repair," Cell Stem Cell. 6;2(3), 2008, 205-13.
Overaman, J.J. et al., "A role for ephrin-A5 in axonal sprouting, recovery, and activity-dependent plasticity after stroke," Proc Natl Acad Sci USA 14;109(33), 2012, E2230-9.
Peppas, N.A., "Hydrogels in biology and medicine: from molecular principles to bionanotechnology," Adv. Materials 18(11), 2006, 1345-1360.
Peppas, N.A. et al., "Hydrogels in pharmaceutical formulations," Eur J Pharm Biopharm. 50(1), 2000, 27-46.
Prestwich, G.D. et al., "Controlled chemical modification of hyaluronic acid: synthesis, applications, and biodegradation of hydrazide derivatives," J Control Release. 30; 53(1-3), 1998, 93-103.
Prestwich, G.D., "Hyaluronic acid-based clinical biomaterials derived for cell and molecule delivery in regenerative medicine," J Control Release. 30; 155(2), 2011, 193-9.
Prestwich, G.D., "The translational imperative: making cell therapy simple and effective," Acta Biomater. 8(12), 2012, 4200-7.
Rieke, E.R. et al., "Sustained subconjunctival protein delivery using a thermosetting gel delivery system," J Ocul Pharmacol Ther. 26(1), 2010, 55-64.
Shu, X.Z. et al., "Attachment and spreading of fibroblasts on an RGD peptide-modified injectable hyaluronan hydrogel," J Biomed Mater Res A. 1;68(2), 2004, 365-75.
Shu, X.Z., "Disulfide cross-linked hyaluronan hydrogels,"Biomacromolecules. 3(6), 2002, 1304-11.
Sreekumar, P.G. et al., "Mechanism of RPE cell death in α-crystallin deficient mice: a novel and critical role for MRP1-mediated GSH efflux," PLoS One. 2012; 7(3), 2012, e33420.
The Writing Committee, Diabetic Retinopathy Clinical R. et al., "Rationale for the diabetic retinopathy clinical research network treatment protocol for center-involved diabetic macular edema," Ophthalmology. 118(12), 2011, e5-14.
Vanderhooft, J.L. et al., "Rheological properties of cross-linked hyaluronan-gelatin hydrogels for tissue engineering," Macromol Biosci. 9;9(1), 2009, 20-8.
Vercruysse, K.P. et al., "Synthesis and in vitro degradation of new polyvalent hydrazide cross-linked hydrogels of hyaluronic acid," Bioconjug Chem. 8(5), 1997, 686-94.
Yang, G., "A cross-linked hyaluronan gel accelerates healing of corneal epithelial abrasion and alkali burn injuries in rabbits," Vet Ophthalmol. 13(3), 2010, 144-50.
Zhang, W., "The use of injectable sonication-induced silk hydrogel for VEGF(165) and BMP-2 delivery for elevation of the maxillary sinus floor," Biomaterials. 32(35), 2011, 9415-24.
Zheng Shu, X. et al., "In situ crosslinkable hyaluronan hydrogels for tissue engineering," Biomaterials. 25(7-8), 2004, 1339-48.
Zhong, J., "Hydrogel matrix to support stem cell survival after brain transplantation in stroke," Neurorehabil Neural Repair. 24(7), 2010, 636-44.
Zustiak, S.P. et al., "Characterization of protein release from hydrolytically degradable poly(ethylene glycol) hydrogels," Biotechnol Bioeng. 108(1), 2011, 197-206.
Ballatori, N. et al., "Glutathione dysregulation and the etiology and progression of human diseases," Biol Chem. 390(3), 2009, 191-214.

* cited by examiner

THIOLATED HYALURONAN-BASED HYDROGELS CROSS-LINKED USING OXIDIZED GLUTATHIONE

This application claims priority to U.S. Provisional Application No. 61/823,322, filed on May 14, 2013, the entire contents of which are hereby incorporated by reference.

FIELD OF THE INVENTION

The field of the invention relates to hyaluronan based hydrogel matrices for in vivo and in vitro applications.

BACKGROUND

The development of biologically derived therapeutics including proteins, cell receptor specific peptides, monoclonal antibodies [58], siRNAs and oligonucleotides designed to inhibit translation of key components of a signal transduction pathway [1, 59, 60], growth factors for improving cellular repair [61], and/or therapeutic cells to rebuild damaged tissues [8, 14, 62] is ongoing. While all biologically derived therapeutics are subject to delocalization after site-specific local injection or application, the macromolecules can be easily degraded by host proteases or ribonucleases. In addition, naked therapeutic cells undergo dramatic cell death such that only <3% cells are present shortly after transplantation [11, 20, 63]. One way to deliver these therapeutics to a specific locus is to mix them with hydrogels which not only protect these biologics and cells due to the polymer pore size, but also provide a lifelike cellular microenvironment rich in hyaluronic acid [21, 57, 64-66].

Hydrogels are three-dimensional hydrophilic, polymeric networks capable of imbibing large amounts of water or biological fluids. The networks may be comprised of homopolymers or copolymers [76]. While being highly hydrophilic, hydrogels are prevented from dissolving due to their chemically or physically crosslinked network. Water or biological fluids can penetrate between the polymer chains of the network causing swelling resulting in hydrogel formation. Hydrogels are appealing for biological applications because of their high water content and their biocompatibility [77]. Synthetic hydrogels provide a delivery vehicle for a wide variety of therapeutics including large molecular weight protein and peptide drugs as well as cellular based therapeutics.

Hydrogels from many synthetic polymers such as poly (hydroxyethyl methacrylate) (PHEMA), poly-(ethylene glycol) (PEG) and poly(vinyl alcohol) (PVA) have been described [77]. Hydrogels created from naturally sourced material such as collagen, hyaluronic acid (HA), fibrin, alginate, agarose and chitosan have also been described [78].

HA is a glycosaminoglycan that is comprised of repeating disaccharide units and is prevalent, for example, during wound healing and in joints. Covalently crosslinked hydrogels formed by various chemical modifications have been described [79-84].

The preclinical use of hydrogels to maintain bioactivity and slow release of biologics has been described [15-19]. Furthermore, hydrogel use in cell delivery has been shown to improve cell viability and localization post-implantation [20-22]. Several different hydrogels have been used as excipients in FDA-approved ocular small molecule therapeutics to increase their residence time on the eye surface [23]. In addition, two new hydrogel formulations have been reported which show promise in delivering therapeutic cells to the subretinal space [6, 24-26]. While some of these formulations are composed of hyaluronic acid to match ocular tissues and maximize biocompatibility, these hydrogels do not have all of the characteristics required for successful delivery of both complex, fragile macromolecules, and cells.

Recently, a hydrogel based on thiol-modified derivatives of hyaluronic acid (HA) and porcine gelatin crosslinked with polyethylene glycol diacrylate (PEGDA) (trade name HyStem®) has been developed to meet these criteria [27, 30-33]. Crosslinked HA hydrogels, including HyStem®, have been successfully used in animal models of corneal epithelial wound healing [25], corneal tissue engineering [5], and retinal repair [7]. Crosslinked HA hydrogels also provide a flexible platform, allowing a user to modulate both gel compliance and gelation time by adjusting the ratio of its components [31, 34]. Since HyStem® gelation times are inversely proportional to final gel stiffness, higher concentrations of the PEGDA crosslinker will cause HyStem to gel in five minutes (G'>1300 Pa) while low concentrations require approximately one to two hours to form softer (G'<50 Pa) gels [31, 34, 35].

There are instances, however, when a modification of the HyStem® hydrogel composition is needed to retain both low compliance and rapid gelation time in a variety of applications. For example, corneal application would benefit from a softer hydrogel that gels within five minutes to prevent washout from the eye surface due to tear turn over and blinking [4, 23]. For example, therapeutic retinal progenitor cells require a low compliance gel to retain function [7]. A quick-gelling hydrogel would also aid in localizing the cells shortly after injection, preventing exudation through the needle track [36].

Thus there is a need for improved HA based hydrogels that can be readily tailored to meet specific applications, including therapeutic applications and the use of hydrogels for delivery of therapeutic agents. There is also a need for improved methods of making HA based hydrogels that provide for greater control of the physical and chemical characteristics of the hydrogel including, but not limited to, in situ gelation speed, cytocompatibility, biocompatibility and capacity to be functionalized. Moreover, there is also a need to simplify the manufacture of hydrogels in a cost effective way. The invention described herein meets these needs as well as other needs in the field.

SUMMARY OF THE INVENTION

In various embodiments described herein the invention provides methods of making hydrogels using oxidized glutathione (GSSG) as a cross-linking agent, as well as methods of using these hydrogels. Various other embodiments described herein provide compositions comprising hydrogels made according to the methods described herein, as well as compositions comprising chemical moieties comprising GSSG and hydrogel components. Yet other embodiments provide kits for making hydrogels using GSSG. Yet other embodiments provide methods of using the hydrogels of the invention for subcutaneous and subconjunctival delivery of therapeutics.

In certain embodiments the invention provides a method of making a hydrogel comprising: 1) contacting a thiolated monomer with GSSG; and 2) allowing the monomer and GSSG to react thereby forming a hydrogel.

In other embodiments the invention provides a method of making a hydrogel comprising: 1) contacting a first thiolated monomer with GSSG; 2) allowing the thiolated monomer and the GSSG react; and 3) adding a second thiolated monomer to the reaction of step 2) thereby forming a hydrogel comprising the first and second thiolated monomer. In some embodiments the first and second thiolated monomer may be the same thiolated monomer. In other embodiments the first thiolated polymer is not the same as the second thiolated monomer.

In further embodiments the invention provides a method of making a hydrogel comprising: 1) contacting thiolated carboxymethylated hyaluronan (CMHA-S) with GSSG; and 2) allowing the CMHA-S and GSSG to react thereby forming a hydrogel.

In yet other embodiments the invention provides a method of making a hydrogel comprising: 1) contacting thiolated carboxymethylated hyaluronan (CMHA-S) with GSSG; 2) allowing the CMHA-S and GSSG to react; and 3) contacting the reaction of step 2 with a thiolated monomer thereby forming a hydrogel comprising CMHA-S and the thiolated monomer. In some embodiments the thiolated monomer is CMHA-S. In other embodiments the thiolated monomer is not CMHA-S.

In some embodiments the invention provides a method of making a hydrogel comprising: 1) contacting thiolated carboxymethylated hyaluronan (CMHA-S) with GSSG; 2) allowing the CMHA-S and GSSG to react; and 3) contacting the reaction of step 2 with CMHA-S thereby forming a hydrogel comprising a multimer of CMHA-S.

In still other embodiments the invention provides a method of making a hydrogel comprising: 1) contacting thiolated carboxymethylated hyaluronan (CMHA-S) with GSSG; 2) allowing the CMEA-S and GSSG to react; and 3) contacting the reaction of step 2 with thiolated porcine gelatin (Gelin®-S) thereby forming a hydrogel comprising CMHA-S and thiolated porcine gelatin (Gelin®-S).

In further embodiments the invention provides a method of making a hydrogel in the steps shown in FIG. 1. In some embodiments the method may further comprise adding a therapeutic agent before the hydrogel polymerizes. In other embodiments the method may further comprise adding a therapeutic agent after the hydrogel polymerizes.

In certain embodiments the invention provides a method of making a hydrogel comprising a therapeutic agent comprising: 1) contacting a thiolated monomer with GSSG and a therapeutic agent; and 2) allowing the monomer, the GSSG and the therapeutic agent to react thereby forming a hydrogel.

In other embodiments the invention provides a method of making a hydrogel comprising a therapeutic agent comprising: 1) contacting a first thiolated monomer with GSSG; 2) allowing the thiolated monomer and the GSSG react; and 3) adding a second thiolated monomer and a therapeutic agent to the reaction of step 2) thereby forming a hydrogel comprising a therapeutic agent and the first and second thiolated monomers. In some embodiments the first and second thiolated monomer may be the same thiolated monomer. In other embodiments the first thiolated polymer is not the same as the second thiolated monomer.

In still further embodiments the invention provides a method of making a hydrogel comprising a therapeutic agent comprising: 1) contacting thiolated carboxymethylated hyaluronan (CMHA-S) with GSSG and a therapeutic agent; and 2) allowing the therapeutic agent, the CMEA-S and GSSG to react thereby forming a hydrogel comprising a therapeutic agent.

In yet other embodiments the invention provides a method of making a hydrogel comprising a therapeutic agent comprising: 1) contacting thiolated carboxymethylated hyaluronan (CMHA-S) with GSSG; 2) allowing the CMHA-S and GSSG to react; and 3) contacting the reaction of step 2 with a thiolated monomer and a therapeutic agent thereby forming a hydrogel comprising a therapeutic agent, CMHA-S and the thiolated monomer. In some embodiments the thiolated monomer is CMHA-S. In other embodiments the thiolated monomer is not CMHA-S.

In some embodiments the invention provides a method of making a hydrogel comprising a therapeutic agent comprising: 1) contacting thiolated carboxymethylated hyaluronan (CMHA-S) with GSSG; 2) allowing the therapeutic agent, the CMHA-S and GSSG to react; and 3) contacting the reaction of step 2 with a therapeutic agent and CMHA-S thereby forming a hydrogel comprising a multimer of CMHA-S and therapeutic agent.

In still other embodiments the invention provides a method of making a hydrogel comprising a therapeutic agent comprising: 1) contacting thiolated carboxymethylated hyaluronan (CMHA-S) with GSSG; 2) allowing the CMHA-S and GSSG to react; 3) contacting the reaction of step 2 with thiolated porcine gelatin (Gelin®-S) and a therapeutic agent thereby forming a hydrogel comprising a therapeutic agent, CMHA-S and thiolated porcine gelatin (Gelin®-S).

In yet further embodiments the invention provides a method of making a hydrogel comprising a therapeutic agent using any of the methods of making hydrogels disclosed infra. The therapeutic agent may be added at any time point in the reaction. Thus the therapeutic agent may be combined with a first component of the hydrogel before any additional reagents are added. Alternatively (or in addition to) the therapeutic agent may be added to the reaction with the second or later component of the hydrogel. The therapeutic agent may be added after the hydrogel has polymerized.

In further embodiments the invention provides a method of making a peptide functionalized hydrogel comprising 1) contacting a monomer comprising a thiol group with a maleimido tagged peptide to form a peptide functionalized monomer; and 2) contacting the peptide functionalized monomer of step 1) with GSSG to form a peptide functionalized hydrogel.

In some embodiments the invention provides a method of making a peptide functionalized hydrogel comprising 1) contacting CMHA-S with a malemido-tagged peptide to form a peptide functionalized CMHA-S and 2) contacting the peptide functionalized CMHA-S of step 1) with GSSG thereby forming a peptide functionalized hydrogel.

In yet other embodiments the invention provides a method of making a hydrogel comprising RGD (arginine-glycine-aspartate) comprising contacting CMHA-S with a malemido tagged peptide comprising RGD to form a peptide functionalized CMHA-S and 2) contacting the functionalized CMHA-S of step 1 with GSSG thereby forming a hydrogel comprising RGD.

In some embodiments the invention provides a maleimido functionalized peptide linked to a thiolated moiety.

In other embodiments the invention provides a maleimido functionalized peptide linked to a thiolated monomer.

In yet other embodiments the invention provides CMHA-S linked with a maleimido-functionalized peptide.

In yet other embodiments, the invention provides a hydrogel comprising CMHA-S and a maleimido-functionalized peptide. In yet other embodiments, the invention provides a hydrogel comprising thiolated gelatin and a maleimido-functionalized peptide.

In certain embodiments the invention provides a peptide functionalized polymer. The peptide may comprise the amino acid sequence RGD.

In some embodiments the invention provides a peptide functionalized CMHA-S.

In still other embodiments the invention provides a peptide functionalized CMHA-S wherein the peptide comprises RGD.

In yet other embodiments the invention provides an RGD peptide functionalized CMHA-S.

In further embodiments the invention provides a hydrogel comprising a polymer functionalized with a peptide.

In some embodiments the invention provides a hydrogel functionalized with a peptide comprising RGD.

In yet other embodiments the invention provides a hydrogel comprising CMHA-S functionalized with a peptide.

In still further embodiments the invention provides a hydrogel comprising CMHA-S functionalized with a peptide comprising RGD.

In yet other embodiments the invention provides a hydrogel comprising CMHA-S functionalized with an RGD peptide.

In further embodiments the invention provides a composition comprising a polymer functionalized with a peptide and a cell. The cell may be attached to the polymer functionalized with the peptide.

In some embodiments the invention provides a composition comprising CMHA-S functionalized with a peptide and a cell. The cell may be attached to the CMHA-S functionalized with the peptide.

In other embodiments the invention provides a composition comprising CMHA-S functionalized with a peptide comprising RGD and a cell. The cell may be attached to the CMHA-S functionalized with a peptide comprising RGD.

In still other embodiments the invention provides a composition comprising CMHA-S functionalized with an RGD peptide and a cell. The cell may be attached to the CMHA-S functionalized with an RGD peptide.

In still further embodiments the invention provides a method of culturing a cell comprising obtaining a hydrogel functionalized with a peptide and contacting the hydrogel with the cell and a suitable culture media thereby culturing a cell. The hydrogel may be made by any of the methods described infra.

In certain embodiments the invention provides a method of culturing a cell comprising obtaining a hydrogel comprising CMHA-S functionalized with a peptide and contacting the hydrogel comprising CMHA-S functionalized with a peptide with a cell and a suitable culture media thereby culturing a cell.

In other embodiments the invention provides a method of culturing a cell comprising obtaining a hydrogel comprising CMHA-S functionalized with a peptide comprising RGD and contacting the hydrogel comprising CMHA-S functionalized with a peptide comprising RGD with a cell and a suitable media thereby culturing a cell.

In still other embodiments the invention provides a method of culturing a cell comprising obtaining a hydrogel comprising CMHA-S functionalized with a RGD peptide contacting the hydrogel comprising CMHA-S functionalized with the RGD peptide with a cell and a suitable culture media thereby culturing a cell.

In further embodiments the invention provides a method of treating a subject in need of therapy comprising making a hydrogel according to any of the methods disclosed infra and administering the hydrogel to the subject in need of therapy.

In yet other embodiments the invention provides a method of treating a subject in need of therapy comprising making a hydrogel comprising a therapeutic agent according to any of the methods disclosed infra and administering the hydrogel comprising a therapeutic agent to the subject in need of therapy.

In still other embodiments the invention provides a method for treating a subject in need of therapy comprising bringing into contact a first thiolated monomer, a second thiolated monomer, GSSG and a therapeutic agent, thereby generating a a hydrogel comprising a therapeutic agent, and administering the hydrogel comprising a therapeutic agent to the subject in need of therapy. In some embodiments the subject in need of therapy has an ocular injury. In some embodiments the therapeutic agent is added before the hydrogel polymerizes; in other embodiments the therapeutic agent is added after the hydrogel polymerizes.

In yet other embodiments the invention provides a method for treating a subject in need of therapy, comprising: 1) obtaining a hydrogel made by any of the methods desctibed infra wherein the hydrogel comprises a therapeutic agent; and 2) administering the hydrogel to the subject.

In further embodimements the invention provides a system for administering a therapeutic agent to a patient, the system comprising a first thiolated monomer, a second thiolated monomer, GSSG and a therapeutic agent. In some embodiments the first thiolated monomer is CMHA-S. In other embodiments the first thiolated monoer is not CMHA-S. In some embodiments the second thiolated monomer is thiolated gelatin. In other embodiments the second thiolated monomer is not thiolated gelatin.

In other emodiments the invention provides a hydrogel comprising a first and a second thiolated monomer cross-linked with GSSG.

In further embodiments the invention provides a method of making a glutathionylated CMHA-S moiety comprising contacting CMHA-S with GSSG; 2) allowing the CMHA-S and the GSSG to react thereby forming a glutathionylated CMHA-S moiety.

In still further embodiments the invention provides a glutathionylated CMHA-S moiety.

In other embodiments the invention provides a hydrogel made by crossing linking a first and second moiety with GSSG. The first and second moiety may be the same moiety or different moieties. The first and second moiety may be a first and second monomer in some embodiments. In other embodiments the first and second moiety may be a peptide. In yet other embodiments the first and second moiety may be a peptide and a monomer. In certain embodiments the hydrogel may further comprise a therapeutic agent.

In further embodiments the invention provides a hydrogel comprising CMHA-S and a second thiolated monomer made by crosslinking the CMHA-S and the second thiolated monomer with GSSG. In some embodiments the second thiolated monomer is CMHA-S. In other embodiments the second thiolated monomer is not CMHA-S. In other embodiments the second thiolated monomer is Gelin-S. The hydrogel may further comprise a therapeutic agent.

In yet other embodiments the invention provides a kit comprising GSSG and one or more thiolated moieties. The thiolated moieties may include one or more thiolated monomers; one or more thiolated peptides or a combination of one or more thiolated monomers and one or more thiolated peptides.

In some embodiments the invention provides a kit comprising a malemido functionalized peptide and thiolated moiety. The thiolated moieties may include one or more thiolated monomers; one or more thiolated peptides or a combination of one or more thiolated monomers and one or more thiolated peptides.

In the embodiments described above polymers may be substituted for monomers in the methods, kits and compositions so recited. Thus, for example, a monomer unit of HA could be substituted with an already polymerized HA.

DESCRIPTION OF DRAWINGS

For a fuller understanding of the nature and advantages of the present invention, reference should be had to the following detailed description taken in connection with the accompanying drawings, in which.

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention which will be limited only by the appended claims. Unless defined otherwise, all technical and scientific terms used herein have the same meanings as commonly understood by one of ordinary skill in the art. Any methods and materials similar or equivalent to those described herein can be used in the practice or testing of embodiments of the present disclosure.

As used herein, the singular forms "a," "an," and "the" include plural reference unless the context clearly dictates otherwise. Thus, for example, reference to a "therapeutic" is a reference to one or more therapeutics and equivalents thereof known to those skilled in the art, and so forth.

As used herein, the term "about" means plus or minus 10% of the numerical value of the number with which it is being used. Therefore, about 50% means in the range of 45% to 55%.

The term "antibody", as used herein, means an immunoglobulin or a part thereof, and encompasses any polypeptide comprising an antigen-binding site regardless of the source, method of production, or other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can bind antigen, for example, an Fab, F (ab')$_2$, Fv, scFv.

The term "carboxymethylated, thiolated hyaluronic acid," as used herein, refers to hyaluronan modified with both a carboxymethyl group and a thiol group (see U.S. Pat. Nos. 7,928,069 and 7,981,871).

The term "crosslinking agent," as used herein, refers to an agent that catalyzes the gel formation but is not part of the final gel.

The term "Glutathione" ("GSH"), as used herein, refers to a tripeptide with a gamma peptide linkage between the amine group of cysteine (which is attached by normal peptide linkage to a glycine) and the carboxyl group of the glutamate side-chain.

Figure 1:
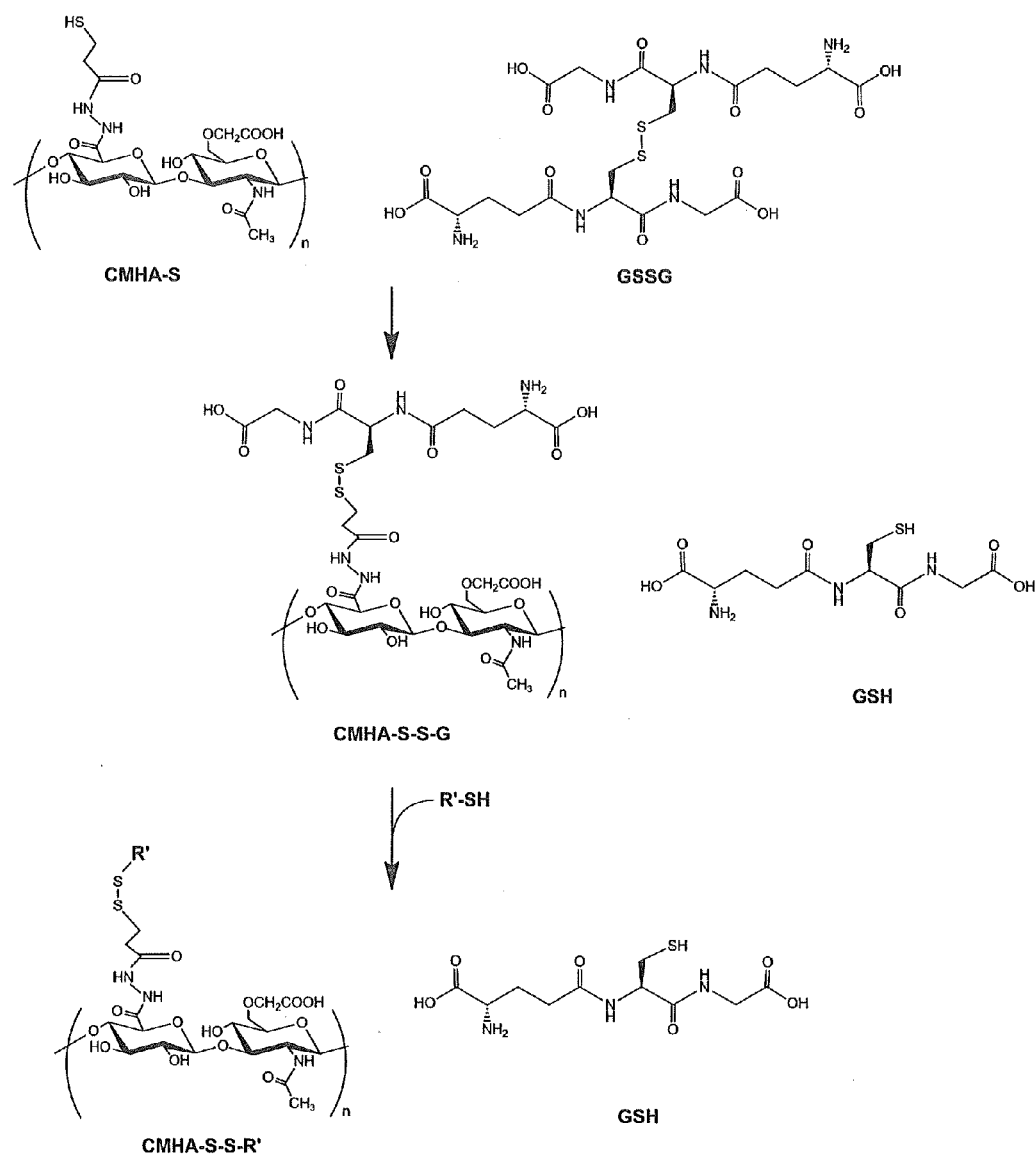
FIG. 1 shows a scheme for Thiol-disulfide exchange reaction for making CMHA/Gelin/GSSG hydrogels.

The term "Oxidized glutathione" (or "glutathione disulfide," "GSSG") refers to two molecules of the tripeptide glutathione (GSH) crosslinked to one another by a disulfide bond between its respective cysteines (FIG. 1).

The term "hyaluronan" "hyaluronic acid" "HA," as used herein, refers to a polymer of disaccharides, composed of D-glucuronic acid and D-N-acetylglucosamine, linked via alternating β-1,4 and β-1,3 glycosidic bonds. It is an anionic, nonsulfated glycosaminoglycan. Hyaluronan can be any length or size. Polymers of hyaluronan can range in size from 5,000 to 20,000,000 Da in vivo.

The term "hydrogel," as used herein, refers to a hydrophilic polymer.

The terms "maleimide" and "maleimido," as used herein, refer to the chemical compound with the formula $H_2C_2(CO)_2NH$. The unsaturated imide is a building block in organic synthesis. The name is a contraction of maleic acid and imide, the —C(O)NHC(O)— functional group. The term "maleimides" also describes a class of derivatives of the parent maleimide where the NH group is replaced with alkyl or aryl groups such as a methyl or phenyl, respectively. The substituent can also be a polymer.

The term "monomer" or "macromonomer" as used herein refers to a chemical moiety that under appropriate conditions can polymerize with itself and/or another moiety to form a polymer. Examples of monomers include HA, CMHA, gelatin and the like. In certain instances the monomer unit can itself be a polymer, e.g. HA is polymer of two disaccharides that can undergo further polymerization.

The use of "nucleic acid," "polynucleotide" or "oligonucleotide" or equivalents herein means at least two nucleotides covalently linked together. In some embodiments, an oligonucleotide is an oligomer of 6, 8, 10, 12, 20, 30 or up to 100 nucleotides. In some embodiments, an oligonucleotide is an oligomer of at least 6, 8, 10, 12, 20, 30, 40, 50, 60, 70, 80, 90, 100, 150, 200, 300, 400, or 500 nucleotides. A "polynucleotide" or "oligonucleotide" may comprise DNA, RNA, cDNA, PNA or a polymer of nucleotides linked by phosphodiester and/or any alternate bonds.

The term "peptide," as used herein, refers to two or more amino acids joined by a peptide bond. A peptide can, in some instances, be a portion of a full length protein.

The term "polymer," as used herein, refers to any of a class of natural or synthetic substances composed of macromolecules that are multiples of monomers. The monomers need not all be the same or have the same structure. Polymers may consist of long chains of unbranched or branched monomers or may be cross-linked networks of monomers in two or three dimensions. Their backbones may be flexible or rigid. Some natural inorganic materials (e.g., the minerals diamond, graphite, and feldspar) and certain man-made inorganic materials (e.g., glass) have polymer-like structures. Many important natural materials are organic polymers, including cellulose (from sugar monomers; polysaccharides), hyaluronan, lignin, rubber. Synthetic organic polymers include many plastics, including polyethylene, the nylons, polyurethanes, polyesters, vinyls (e.g., PVC), and synthetic rubbers.

By "pharmaceutically acceptable", it is meant the carrier, diluent or excipient must be compatible with the other ingredients of the formulation and not deleterious to the recipient thereof.

The term "subject," as used herein includes, but is not limited to, humans, non-human primates and non-human vertebrates such as wild, domestic and farm animals including any mammal, such as cats, dogs, cows, sheep, pigs, horses, rabbits, rodents such as mice and rats. In some embodiments, the term "subject," refers to a male. In some embodiments, the term "subject," refers to a female.

"Therapeutic Agent," as used herein, refers to any agent administered to a subject to treat a condition, including but not limited to a molecule such as a small molecule, a moiety, a peptide, a protein, a lipid, a polysaccharide, a nucleic acid, an antibody, a cell, a hormone, a growth factor.

The term "suitable media," as used herein, refers to a solution that can be used to grow cells in culture. A suitable media may include a formulation of salts and/or buffering reagents. A suitable media may include any or all of the following: salts, sugars, amino acids, proteins, growth factors, cytokines, hormones, additives such as serum, albumin, antibiotics, insulin, selenium and transferrin. Suitable culture media includes for example commercially available culture media such as DMEM, MEM Stem Pro and the like.

A "therapeutically effective amount" of a composition such as a therapeutic agent is a predetermined amount calculated to achieve the desired effect. In some embodiments, the effective amount is a prophylactic amount. In some embodiments, the effective amount is an amount used to medically treat the disease or condition. The specific dose of a composition administered according to this invention to obtain therapeutic and/or prophylactic effects will, of course, be determined by the particular circumstances surrounding the case, including, for example, the composition administered, the route of administration, and the condition being treated. It will be understood that the effective amount administered will be determined by the physician in the light of the relevant circumstances including the condition to be treated, the choice of composition to be administered, and the chosen route of administration. A therapeutically effective amount of composition of this invention is typically an amount such that when it is administered in a physiologically tolerable excipient composition, it is sufficient to achieve an effective systemic concentration or local concentration in the targeted tissue.

The term "Thiolated hyaluronan" refers to hyaluronan modified with a thiol group (see U.S. Pat. Nos. 7,928,069 and 7,981,871).

The term "Thiolated Gelatin" or "Thiolated Porcine Gelatin," as used herein refers, to a gelatin molecule functionalized with a thiol group (see U.S. Pat. Nos. 7,928,069 and 7,981,871).

The terms "treat," "treated," or "treating," as used herein, can refer to both therapeutic treatment or prophylactic or preventative measures, wherein the object is to prevent or slow down (lessen) an undesired physiological condition, symptom, disorder or disease, or to obtain beneficial or desired clinical results. In some embodiments, the term may refer to both treating and preventing. For the purposes of this disclosure, beneficial or desired clinical results may include, but are not limited to one or more of the following: alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response. Treatment also includes prolonging survival as compared to expected survival if not receiving treatment.

The term "tissue" refers to any aggregation of similarly specialized cells that are united in the performance of a particular function.

The term "thiol" as used herein, refers to an organosulfur compound that contains a carbon-bonded sulfhydryl (—C—SH or R—SH) group (where R represents an alkane, alkene, or other carbon-containing group of atoms). A "thiolated molecule," as used herein, can refer to either the reduced (SH) or oxidized (S—S) form of the group.

Methods of Making Hydrogels

In certain embodiments the invention provides methods of making hydrogels that is fast, effective, easy to perform and inexpensive, but also allows for the control of hydrogel parameters such as gel time, elastic modulus, pore size and the like. The method comprises using GSSG as an oxidizing agent for monomers and/or polymers having a one or more thiol groups. In some embodiments the target monomer or polymer comprises a plurality of thiol groups. Any polymer comprising a thiol group may be used. Examples of suitable polymers include natural polymers such as chitin, hyaluronan, alginate, gelatin and the like. In some embodiments the polymer may be modified with a peptide, such as a peptide functionalized with a thiol reactive group. For example the peptide may be functionalized with a maleimide group. The peptide may comprise the amino acid sequence RGD.

Hydrogels may be prepared by dissolving the components of the hydrogel in water or a suitable buffer. Components may include one or more monomers, and an oxidizing agent. Examples of monomers include HA, gelatin, CMHA-S and GSSG. A suitable buffer may include PBS for example. The buffer may be at a pH of about 7, e.g. 7.4. The buffer may range from about 6.5 to about 8, from about 6.8 to about 7.8, from about 6.9 to about 7.6. The components may be combined into a single buffer or alternatively the monomers can be solubilized in one buffer and the reducing agent can be solubilized separately. The polymer solution can be combined with the oxidizing agent subsequently to control the time and rate of polymerization.

The concentration of the components of the hydrogel may be varied according to the desired parameters of the hydrogel. For example higher concentrations of monomer and/or oxidizing agent may result in a stiffer denser hydrogel. Lower concentrations of monomer and or oxidizing agent may provide for softer less dense hydrogels with higher water content.

In some embodiments the working concentration (working solutions) of CMHA-S solution used in the methods described infra may range from about 0.1% (w/v) to about 5% (w/v); from about 0.2% (w/v) to about 4% (w/v); from about 0.3% (w/v) to about 3% (w/v); from about 0.4% (w/v) to about 2% (w/v). In some embodiments the concentration of CMHA-S is about 0.4% (w/v); about 0.8% (w/v); about 1.6% (w/v).

In some embodiments the working concentration (working solutions) of thiolated gelatin used in the methods described infra may range from about 0.1% (w/v) to about 5% (w/v); from about 0.2% (w/v) to about 4% (w/v); from about 0.3% (w/v) to about 3% (w/v); from about 0.4% (w/v) to about 2% (w/v). In some embodiments the concentration of thiolated gelatin used is about 0.4% (w/v).

In some embodiments the working concentration (working solution) of GSSG used in the methods described infra ranges from about 0.1 mM to about 50 mM; from about 0.3 mM to about 30 mM; from about 0.5 mM to about 25 mM; from about 1 mM to about 20 mM. In some embodiments the concentration of GSSG used is about 1 mM, about 2 mM, about 3, mM, about 4 mM, about 5 mM, about 6 mM, about 7 mM, about 8 mM, about 9 mM, about 10 mM, about 15 mM, about 20 mM.

The working solutions of the monomers, e.g. CMHA-S and thiolated gelatin may be mixed at any desired concentration to form the macromonomer solution. For example a 1:1 solution of CMHA-S and thiolated gelatin may be used. The working solutions may be mixed at a 2:1, 3:1, 4:1 5:1 of CMHA-S to thiolated gelatin. The working solutions may be mixed at a 2:1, 3:1, 4:1, 5:1 of thiolated gelatin to CMHA. Once the working solutions have been combined the oxidizing agent may be added. Alternatively the oxidizing agent can be added to a first monomer and then a second or subsequent monomer may be added. The oxidizing agent, e.g. GSSG may be added at about 0.5 volume of GSSG working solution to about 10 volumes of the macromonomer solution; at about 0.9 volume of GSSG to about 8 volumes of macromonomer solution; at about 1 volume of GSSG to about 4 volumes of macromonomer solution.

In certain embodiments the shear elastic modulus of the hydrogel ranges from about 5 Pa to about 1000 Pa; from about 10 Pa to about 900 Pa; from about 9 Pa to about 800 Pa. In some embodiments the shear elastic modulus is about 5 Pa, about 10 Pa, about 15 Pa; about 20 Pa, about 25 Pa, about 30 Pa, about 35 Pa about 40 Pa, about 50 Pa, about 60 Pa, about 70 Pa, about 80 Pa, about 90 Pa, about 100 Pa, about 300 Pa, about 500 Pa, about 700 Pa.

In some embodiments one or more of the monomers may be functionalized. The monomer may be functionalized with any suitable moiety. In some embodiments the monomer is functionalized with a peptide. The functionalized monomer may include a moiety comprising a maleimido group. The maleimide group can undergo a Michael addition reaction by reacting with a thiolated monomer as described infra.

Hydrogel Properties

In certain embodiments the invention provides hydrogels that have all of the characteristics required for successful delivery of complex, fragile macromolecules, and cells.

The desired hydrogel may contain cellular attachment sites to prevent anoikis of anchorage-dependent cells [11]. They also may have functionalizable groups on its component biopolymers allowing not only the one-step covalent linking of macromolecular therapeutic cargo by the user, but also provide for matrix customization for specific cell types requiring a unique collection of cellular attachment sites [27, 28]. Finally, the hydrogels described infra may have validated and desired syringeability with the gauge of the needle determined by the placement location. For example, intravitreal delivery requires injection through a 30 g needle commonly used by ophthalmologists [6, 29]. These properties may be achieved by varying the concentration of one or more of the monomers and/or the oxidizing agent.

Recently, a hydrogel based on thiol-modified derivatives of hyaluronic acid (HA) and porcine gelatin crosslinked with polyethylene glycol diacrylate (PEGDA) (trade name HyStem®) has been developed to meet these criteria [27, 30-33]. Crosslinked HA hydrogels, including HyStem®, have been successfully used in animal models of corneal epithelial wound healing [25], corneal tissue engineering [5], and retinal repair [7]. It is also a flexible platform, allowing a user to modulate both gel compliance and gelation time by adjusting the ratio of its components [31, 34]. Since HyStem gelation times are inversely proportional to final gel stiffness, higher concentrations of the PEGDA crosslinker will cause HyStem to gel in five minutes (G'>1300 Pa) while low concentrations require approximately one to two hours to form softer (G'<50 Pa) gels [31, 34, 35].

There are instances however when a modification of the HyStem hydrogel composition is needed to retain both low compliance and rapid gelation time, for example, in ophthalmic applications. For example, corneal application would benefit from a softer hydrogel that gels within five minutes to prevent washout from the eye surface due to tear turn over and blinking [4, 23]. Importantly, therapeutic retinal progenitor cells require a low compliance gel to retain function [7]. A quick-gelling hydrogel would also aid in localizing the cells shortly after injection, preventing exudation through the needle track [36].

In order to alter the gelation profile, an alternative is to crosslink the two thiolated HyStem biopolymers through disulfide bonds using the thiol-disulfide exchange reaction with a physiologically relevant disulfide-containing molecule [37] (FIG. 1). Oxidized glutathione (or glutathione disulfide, GSSG) is composed of two molecules of the tripeptide glutathione (GSH) crosslinked to one another by a disulfide bond between its respective cysteines (FIG. 1). GSH and GSSG are key players in normal cellular thiol metabolism and together account for most of the nonprotein sulfur of a cell [38, 39]. GSSG has a history of use in humans, both as a component of the intraocular irrigation solution BSS Plus® and as a systemically administered drug candidate [40]. In addition, after thiol-disulfide exchange, GSSG is converted to glutathione, a reductant crucial in maintaining the health of the lens, cornea, aqueous humor, and retina of the aging eye [41, 42]. Provided herein are gels made by GSSG based thiol-disulfide exchange reaction with the multiple thiol groups of the thiolated HA derivative CMHA-S, causing gelation to occur in less than five minutes and resulting in softer gels that may have general utility for cell-based therapeutics, such as in the eye and other sensitive tissues. The hydrogels described herein provide for the cytocompatibility, biocompatibility, and the ability of this hydrogel system to be functionalized with peptides.

Hydrogel Applications

The hydrogels described infra may be used in vitro and in vivo. In vitro uses include research applications including in vitro cell culture, drug discovery and toxicity study. For example the hydrogels may be used to study the kinetics of drug release. The hydrogels may be used to study the effects of drug release over time on the metabolic activity of a test cell or tissue. The hydrogels described infra may be used to study cell growth, cell viability, and cell morphology in vitro.

The hydrogels described infra may have a therapeutic agent, or a cell linked to or enclosed in the hydrogel. The therapeutic agent or cell may be covalently bound to one or more components of the hydrogel. The therapeutic agent may be non-covalently bound to the hydrogel, e.g., the therapeutic agent may be bound by ionic interactions, hydrogen bonding, or van der Waals forces. The therapeutic agent may be encased within the hydrogel disclosed infra.

Examples of therapeutic agents include small molecules, biologics, peptides, proteins, and nucleic acids (including cDNA, RNA, siRNA, PNA and the like). Therapeutic agents may include, but are not limited to antibiotics, anti-virals, anti-cancer drugs, growth factors, hormones, cytokines, anti-inflammatory drugs, nervous system modulators, pain relievers, narcotics and antibodies.

Examples of cellular agents that may be used with the hydrogels disclosed infra include cells derived in vitro from stem cells. Stem cells include embryonic stem cells, induced pluripotent stem cells, adult stem cells such as mesenchymal stem cells and adipose derived stem cells. Cells derived from stem cells include cellular progenitor cells (i.e. cells that have not completely matured into an adult phenotype) and fully developed mature adult cells. Cell types include cells of endodermal origin, ectodermal origin and mesodermal origin. Specific cell types may include, but are not limited to cells of the central nervous system such as neurons including dopaminergic neurons, glial cells and astrocytes, cells of the digestive system such as adipose cells, hepatocytes, pancreatic cells including β-islet cells, retinal pigmented epithelial cells, adipose cells and the like.

Where the therapeutic agent is a cell, the cell may attach to the gelatin portion of the hydrogel. Alternatively the cell may be attached to a functionalized monomer within the hydrogel, such as peptide functionalized monomer. Suitable peptides may comprise the RGD sequence. The monomer may be CMHA-S.

The hydrogels described infra may be implanted in a subject requiring treatment. For example the hydrogels may be implanted in the eye to treat corneal epithelial wound healing, to provide corneal tissue engineering, and to provide retinal repair. The hydrogels of the invention can be implanted in the central nervous system of a subject to treat conditions such as stroke, Parkinson's disease, spinal cord injury, MS and the like. The hydrogels can be implanted in the digestive tract or under the kidney capsule to treat conditions such as diabetes or liver disease. The hydrogels can be implanted in the heart to treat conditions such as heart failure, arrhythmia and the like.

Pharmaceutical Compositions and Modes of Administration

Modes of administration for a therapeutic (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Hydrogels as described herein may be administered as a three dimensional construct or as film. In some embodiments the components of the hydrogel may be administered simultaneously as a liquid and allowed to polymerize in vivo. In other embodiments the components of the hydrogel may be combined ex vivo, allowed to polymerize and then administered to the subject as a pre-formed hydrogel.

The therapeutic of the present disclosure can be formulated as a depot preparation. Such long acting formulations can be administered by implantation (for example subcutaneously or intramuscularly) or by intramuscular injection. In some embodiments the composition may be administered by intra-peritoneal injection. In some embodiments the therapeutic disclosed herein can be administered using a catheter.

Depot injections can be administered at about 1 to about 6 months or longer intervals. Thus, for example, the compositions can be formulated with suitable polymeric or hydrophobic materials (for example as an emulsion in an acceptable oil) or ion exchange resins, or as sparingly soluble derivatives, for example, as a sparingly soluble salt.

In transdermal administration, the compositions of the present disclosure, for example, can be applied to a plaster, or can be applied by transdermal, therapeutic systems that are consequently supplied to the subject.

Specific modes of administration will depend on the indication. The selection of the specific route of administration and the dose regimen is to be adjusted or titrated by the clinician according to methods known to the clinician in order to obtain the optimal clinical response. The amount of therapeutic to be administered is that amount which is therapeutically effective. The dosage to be administered will depend on the characteristics of the subject being treated, e.g., the particular subject treated, age, weight, health, types of concurrent treatment, if any, and frequency of treatments, and can be easily determined by one of skill in the art (e.g., by the clinician).

Pharmaceutical formulations containing the therapeutic agent of the present disclosure and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or copolymer of the present disclosure. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The compositions of the present disclosure can be formulated for parenteral administration by injection, e.g., by bolus injection or continuous infusion. The compositions can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the compositions can be formulated readily by combining the therapeutic with pharmaceutically acceptable carriers well known in the art. Such carriers enable the therapeutic of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active therapeutic doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active therapeutic can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the pharmaceutical compositions can take the form of, e.g., tablets or lozenges formulated in a conventional manner.

For administration by inhalation, the therapeutic for use according to the present disclosure is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the therapeutic and a suitable powder base such as lactose or starch.

The compositions of the present disclosure can also be formulated in rectal compositions such as suppositories or retention enemas, e.g., containing conventional suppository bases such as cocoa butter or other glycerides.

Pharmaceutical compositions can include suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The compositions of the present disclosure can also be administered in combination with other active ingredients, such as, for example, adjuvants, protease inhibitors, or other compatible drugs or compounds where such combination is seen to be desirable or advantageous in achieving the desired effects of the methods described herein.

In some embodiments, the disintegrant component comprises one or more of croscarmellose sodium, carmellose calcium, crospovidone, alginic acid, sodium alginate, potassium alginate, calcium alginate, an ion exchange resin, an effervescent system based on food acids and an alkaline carbonate component, clay, talc, starch, pregelatinized starch, sodium starch glycolate, cellulose floc, carboxymethylcellulose, hydroxypropylcellulose, calcium silicate, a metal carbonate, sodium bicarbonate, calcium citrate, or calcium phosphate.

In some embodiments, the diluent component may include one or more of mannitol, lactose, sucrose, maltodextrin, sorbitol, xylitol, powdered cellulose, microcrystalline cellulose, carboxymethylcellulose, carboxyethylcellulose, methylcellulose, ethylcellulose, hydroxyethylcellulose, methylhydroxyethylcellulose, starch, sodium starch glycolate, pregelatinized starch, a calcium phosphate, a metal carbonate, a metal oxide, or a metal aluminosilicate.

In some embodiments, the optional lubricant component, when present, comprises one or more of stearic acid, metallic stearate, sodium stearylfumarate, fatty acid, fatty alcohol, fatty acid ester, glycerylbehenate, mineral oil, vegetable oil, paraffin, leucine, silica, silicic acid, talc, propylene glycol fatty acid ester, polyethoxylated castor oil, polyethylene glycol, polypropylene glycol, polyalkylene glycol, polyoxyethylene-glycerol fatty ester, polyoxyethylene fatty alcohol ether, polyethoxylated sterol, polyethoxylated castor oil, polyethoxylated vegetable oil, or sodium chloride.

Kits

The instant invention also provides kits for use in making hydrogels as described infra. The kits may contain the components of the hydrogels, one or more containers and optionally instructions for making the hydrogels. The kits may contain one or more thiolated monomers and one or more oxidizing agents. Suitable monomers include, for example, CMHA-5, thiolated gelatin. The kit may also include peptides, such as RGD containing peptides to modify one or more of the monomers in the kit. The peptide can be functionalized with a maleimide group to allow the peptide to link to one of the thiolated monomers. The components of the kit may be provided in solution. The solution may include a suitable buffer such as PBS or the components may be provided dissolved in water. Alternatively, the components may be provided as lyophilized reagents. One or more buffers or solutions may be provided in separate containers to solubilize the lyophilized components.

EXAMPLES

The following examples are not intended to limit the scope of what the inventors regard as their invention nor are they intended to represent that the experiments below are all or the only experiments performed.

Materials

Thiolated hyaluronan (Glycosil®, CMHA-S or carboxymethylated, thiolated hyaluronic acid), thiolated porcine gelatin (Gelin-S®), and polyethylene glycol diacrylate (PEGDA) MW 3400 (Extralink®) were obtained from BioTime Inc. (Alameda, Calif.). 4-arm PEG-thiol (MW 20,000) was from Creative PEGworks (Winston Salem, N.C.). Oxidized glutathione, sodium salt (GSSG), reduced glutathione (GSH), L-cystine, D-cystine, oxidized DTT, potassium phosphate, acetonitrile, propidium iodide, and 2-nitro-5-thiosulfobenzoate (NTSB) were purchased from Sigma-Aldrich (St. Louis, Mo.). Phosphate-buffered saline (PBS) was from Fisher (Houston, Tex.). AlamarBlue®, Calcein AM, and Live Dead cell viability assay were obtained from Life Technologies (Carlsbad, Calif.). Peptides were synthesized by Anaspec, Inc. (Sunnyvale, Va.). Collagenase A type I was obtained from Worthington Biochemical (Lakewood, N.J.). Bone marrow-derived mesenchymal stem cells (BM-MSC) were purchased from Lonza (Walkersville, Md.).

GSSG solution was varied to determine effect of its concentration on hydrogel properties described in Table 1). After the solution was thoroughly mixed, gels formed in about 3-5 min (these hydrogels are referred to as CMHA/Gelin/GSSG hydrogels). For hydrogels with Gelin-S omitted (CMHA/GSSG hydrogels), one volume GSSG solution was added to four volumes of thiolated hyaluronic acid (CMHA-S) (1% w/v) solution and thoroughly mixed. Hydrogels containing CMHA-S, Gelin-S, and PEGDA were prepared as per manufacturer's instructions and are referred to as HyStem-C hydrogels.

Initially we tested whether GSSG would be a suitable reactant for a thiol-disulfide exchange reaction with thiolated biopolymers CMHA-S and Gelin-S to form a two-component (CMHA/Gelin/GSSG) gel with no additional crosslinking molecule (FIG. 1 where R'—SH represents Gelin-S). A gel formed in approximately three minutes using a final concentration of 4 mM GSSG and 0.4% w/v CMHA-S and 0.4% w/v Gelin-S (Sample 4, Table 1). Other disulfide containing small molecules tested, such as cysteine and oxidized DT, did not cause gel formation [45].

TABLE 1

Hydrogel Stiffness and Gelation Onset

| Sample | CMHA-S (%) | Gelin-S (%) | GSSG (mM) | Gelation (min) | G' (Pa) | SD (Pa) | q | SD |
|---|---|---|---|---|---|---|---|---|
| 1 | 0.4 | 0.4 | 1 | 5.4 | 9.3 | 2 | | |
| 2 | 0.4 | 0.4 | 2 | 3.2 | 28 | 2 | | |
| 3 | 0.4 | 0.4 | 3 | 3.2 | 33 | 3 | | |
| 4 | 0.4 | 0.4 | 4 | 3.4 | 30 | 1 | 65.5 | 4.9 |
| 5 | 0.4 | 0.4 | 7 | 3.0 | 37 | 4 | | |
| 6 | 0.4 | 0.4 | 10 | 3.0 | 27 | 5 | | |
| 7 | 0.4 | 0.4 | 20 | >60 | 9.3 | 2 | | |
| 8 | 0.8 | 0 | 4 | 12.4 | 94 | 17 | 76.6 | 5.5 |
| 9 | 1.6 | 0 | 4 | 1.1 | 750 | 31 | | |

Analytical Instrumentation

HPLC data were obtained using a Waters 1525 HPLC pump system using a waters 2489 UV/VIS detector (Milford, Mass.) and a Phenomenex Synergi Hydro-RP 80A C18 HPLC Column and Phenomenex SecurityGuard AQ C18 cartridge (Torrance, Calif.). Parallel Plate Rheometry measurements were made on a Bohlin CVO100 rheometer using a 20 mm upper plate (Malvern, Worcestershire, UK). Viscometry measurements were recorded on a Brookfield DV-II+ Pro viscometer using a CPE-40 flat spindle (Middleboro, Mass.). Cell proliferation and viability were determined using Alamar Blue (ex/em 570/585) and Live/Dead Assays (ex/em 494/517) (Life Technologies, Inc., Carlsbad, Calif.) and were recorded using a BioTek Synergy HI Microplate Reader (Winooski, Vt.). Fluorescent images of viable cells were recorded using a Nikon Eclipse TE2000-U microscope (Melville, N.Y.).

Example 1: Preparation of Hydrogels

For Gelin-S containing hydrogels, CMHA-S and Gelin-S were dissolved in sterile degassed water to give 1.0% (w/v) solutions pH 7.4 according to manufacturer's instructions (Hystem®) (BioTime, Inc. Alameda, Calif.). GSSG was resuspended in 1xPBS (pH 7.2) to make a 20 mM solution and filtered through a 0.22 micron syringe filter. The CMHA-S and Gelin-S solutions were mixed in a 1:1 (v:v) ratio (the thiolated macromonomer solution). One volume of the GSSG solution was added to four volumes of the thiolated macromonomer solution (the concentration of Example 2: HPLC Analysis and Equilibrium Constant Calculation CMHA/Gelin/GSSG hydrogels (500 µl) were prepared in triplicate in 24-well plates either with GSSG at different concentrations as described above or with Extralink® (per manufacturer's instructions). After overnight curing in the covered plate at room temperature, 500 µl of 1xPBS (7.2) was added to the top of each gel and incubated in a 37° C. shaker (150 rpm) for 4 hr. After four-hour extraction, 80% of the GSH partitioned to the PBS fraction (data not shown). Each supernatant (50 µl) was then manually injected into the HPLC column. Standard curves with different concentrations of GSSG and GSH showed the linear range of the curve to be between 0.1 mM and 10 mM for both species respectively (data not shown). Flow rate for HPLC was maintained constant at 1.2 ml/min. Buffers used were as follows: HPLC Buffer A: 20 mM Potassium Phosphate (monobasic) adjusted to pH 2.7 with phosphoric acid; and HPLC Buffer B: 100% acetonitrile. The solvent gradient used was as follows: Initial solvent conditions were 98% A, 2% B run at 1.2 ml/min for 15 min. A linear gradient to 20% A, 80% B was run over the period from 15 to 35 min. From 35 to 40 min, the conditions were maintained at 20% A, 80% B and returned to 98% A, 2% B from 40 to 43 min. Equilibration time for the next run was 7 min. To calculate the amount of GSH and GSSG extracted from each hydrogel, the quantities derived from the standard curve were multiplied by 2.5 to correct for both incomplete (80%)

extraction and for dilution of eluted molecules after partitioning from the hydrogel into an equal volume of PBS. The concentrations for all reactants and products were then inserted into the equilibrium constant equation: K=[S—S][GSH]$^2$/[biopolymer thiols]$^2$-[GSSG] where the concentration of disulfide bonds produced after gelation is assumed to be one-half that of the resulting GSH based on the thiol-disulfide exchange reaction stoichiometry.

The thiol-disulfide exchange reaction predicts GSH to be one of the major end products of the reaction (FIG. 1). In order to characterize the thiol-disulfide exchange reaction, the levels of both GSSG remaining and GSH produced after the gelation reaction were measured at three initial GSSG concentrations shown to cause hydrogel stiffness to increase (2, 4, 7 mM) (Table 2). With increasing GSSG concentrations, 3.3 to 4 mM GSH was generated (Table 2). As expected, hydrogels formed by crosslinking with Extralink® (BioTime, Inc. Alameda, Calif.) generated no GSH (data not shown). Since the resulting GSH concentration was double the concentration of the resulting S—S bonds (FIG. 1), the concentration of S—S bonds in the gel also increased minimally from 1.6 mM to 2.0 mM and was mirrored by small increases in hydrogel stiffness (See Tables 1, 2). The remaining unreacted GSSG however significantly increased with increasing GSSG reactant from 0.14 mM to 5.4 mM (Table 2).

TABLE 2

GSH and GSSG Levels in Hydrogels

| Initial [SH] | Initial [GSSG] | Final [S—S] | Final [GSH] | Final [GSSG] | $K_{eq}$ |
|---|---|---|---|---|---|
| 0.0041 | 0.002 | 0.0016 | 0.0033 | 0.0001 | 0.52 |
| 0.0041 | 0.004 | 0.0020 | 0.0040 | 0.0019 | 0.48 |
| 0.0041 | 0.007 | 0.0019 | 0.0038 | 0.0054 | 0.23 |

Notes:
Reactant and Product concentrations before and after thiol-disulfide exchange reaction with oxidized glutathione. Acronyms: Initial [SH], the concentration of thiols from all biopolymers pre-gelation; Initial [GSSG], molar oxidized glutathione concentration pre gelation; Final [S—S], concentration of disulfide bonds post gelation; Final [GSH], final reduced glutathione concentration post gelation; Final [GSSG], final oxidized glutathione concentration post gelation; Keq, calculated equilibrium constant.

Example 3: Equilibrium Mass Swelling Ratio Determination

First, a 0.5 ml aliquot of each hydrogel formulation was gelled in the bottom of quadruplicate 5 ml round-bottom 12×75 mm plastic culture tubes. Then, 3 ml of PBS was added on top of each gel, and the tubes were placed into an incubator at 37° C. and agitated at 150 rpm for 2 hours. The PBS buffer was changed with distilled water and incubated for an additional 2 hours. The hydrogels plus the tubes were weighed after carefully removing the surface buffer at each time point. The mass of the swollen hydrogels was calculated by subtracting the mass of the tube from the total mass. The mass of the dry hydrogel components was calculated by subtracting the mass of the tube from the total mass, which was obtained after the hydrogels were lyophilized. The equilibrium mass swelling ratio (q) was defined as a ratio of the mass of swollen hydrogel to the mass of dry hydrogel.

The equilibrium constant for the reaction decreased significantly above 4 mM GSSG initial concentration. Taken together, this data suggests that many of the free thiols have been glutathionylated using 7 mM GSSG and are unable to participate in completing the thiol-disulfide exchange (Table 2) [49].

Example 4: Physical Property Analysis

Parallel Plate Rheometry: Hydrogels were poured to about 3 mm thickness in 20 mm dishes and allowed to cure in a covered chamber at room temperature for 18 hr. Oscillatory shear measurements of the elastic modulus (G') were then measured at oscillation frequency 1 Hz in a stress sweep test from 0.6 to 20 Pa.

Since modulation of hydrogel stiffness may be relevant for regulating cell behavior and for growth factor release profile [46-48], multiple gels were cast using different GSSG concentrations and then characterized for rheological properties and for the onset of gelation. As the GSSG concentration increases from 1 mM to 20 mM final concentration in the hydrogel mixture before gelation, the shear elastic modulus increases from G' 9.3 Pa (1 mM GSSG) to a maximum of 37 Pa (7 mM GSSG) and then decreases back to G' 9.3 (20 mM GSSG) [49]. The onset of gelation followed a similar pattern, with a longer gelation onset at the extreme GSSG concentrations (5.4 min at 1 mM and greater than 2 hr at 20 mM GSSG) and gelation at 3.0 to 3.4 minutes for the 2 to 10 mM GSSG concentrations (Table 1). At 4 mM GSSG, the equilibrium mass swelling ratio was 65.5 (Sample 4, Table 1).

CMHA/GSSG hydrogels were also prepared with a constant final concentration of GSSG (4 mM). When CMHA-S concentration was doubled to maintain a constant amount of biopolymer (0.8% w/v), shear elastic modulus increased nearly three-fold (G' 94 Pa) and equilibrium mass swelling ratio increased to 76.6 compared to Gelin-S containing hydrogels but onset of gelation slowed by nearly four fold (12.4 min) (Sample 8, Table 1). When the concentration of CMHA-S was again doubled to 1.6% w/v, G' increased nearly an additional eight-fold (750 Pa) and gelation onset was more than a magnitude faster (1.1 min) (Sample 9, Table 1). The data is consistent with previous data showing CMHA-S to be a main driver of gel stiffness [34]. From the data with CMHA/Gelin/GSSG gels, inclusion of Gelin-S speeds gelation and can be explained by Gelin-S five-fold smaller molecular weight than that of CMHA-S [34]. This size difference corresponds to a five-fold increase in diffusivity [50].

Example 5: Viscometry

After mixing all components, 500 µl of the solution was added to the bottom stationary plate of a cone-plate viscometer in order to measure the onset of gelation. In situ gelation of different hydrogel formulations was measured at room temperature at uniform shear rate of 7.5 Hz. The timing of gelation onset occurs when the viscosity of the solution begins to rapidly increase. Gelation time determined by this method showed that the gelation time varies from 1 min to greater than 1 hr (Table 1).

Example 6: Cytocompatibility Studies

ADSC Isolation and Culture:
Stromal vascular fraction (SVF) was isolated from human lipoaspirate as described [43]. To isolate the adherent cellular fraction for in vitro studies, SVF was incubated overnight at 37° C./5% CO2 in control medium (DMEM, 10% FBS, 1% antibiotic/antimycotic solution) on plastic tissue culture plates. Following incubation, the plates were washed extensively with PBS and the remaining adherent cell population (adipose derived stem cells (ADSC)) were maintained at 37° C./5% CO2 in noninductive control medium. To prevent spontaneous differentiation, cells were maintained at subconfluent levels.

3D Cell Culture:

ADSCs (passage 4) were suspended in CMHA-S and Gelin-S containing hydrogels prepared with either Extralink (final PEGDA concentration 0.4% w/v) or GSSG (final concentration 4 mM) at a concentration of 2 million cells per ml. 25 µl was dispensed into the center of each well of a 6-well plate resulting in a thin 10 mm diameter disc attached to the center of the well. The cell hydrogel suspension was allowed 1 hour to polymerize before being covered with culture medium (DMEM/10% FBS). As a control, 25 µl was dispensed into additional plates, but was promptly diluted with complete culture medium allowing the cells to disperse and attach to the tissue culture surface. At days 1, 3, 7, and 10, the cultures were analyzed for viability with Alamar Blue according to the provided instructions. Briefly, the medium was removed and replaced with 1 ml of a 10% Alamar Blue solution in culture medium. After incubation for 4 h, a 100 µl sample was drawn from each well and its fluorescence measured. Fluorescence staining and microscopy was also performed using Calcein AM to visualize viable cells and propidium iodide to observe non-viable cells. Proliferation data was corrected for cell number and normalized to that of the hydrogels prepared with GSSG.

Figure 2:
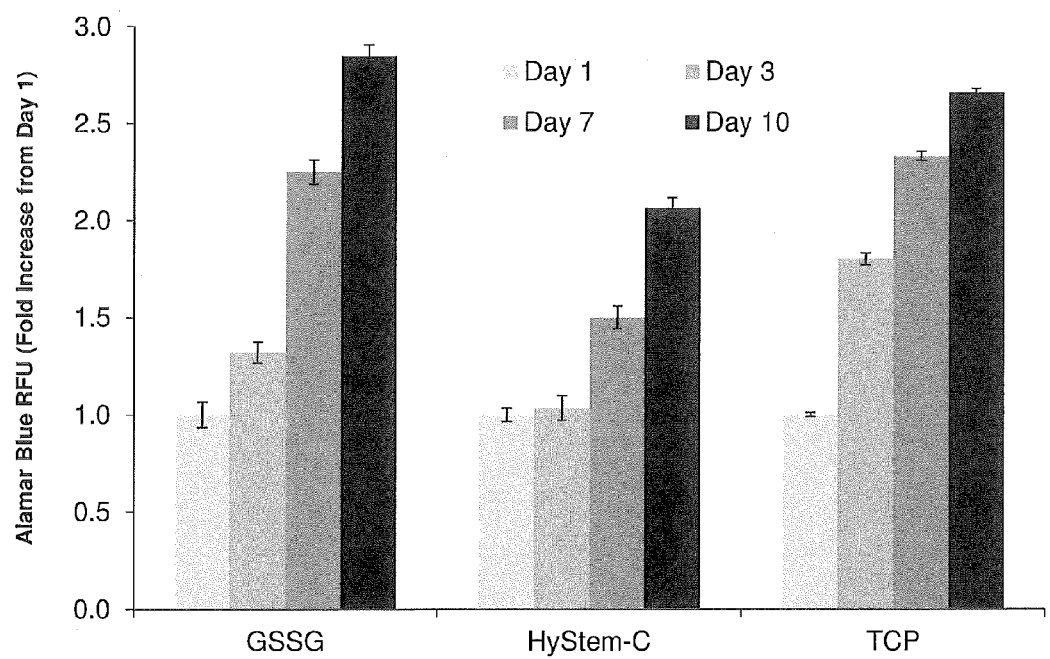
FIG. 2 is a graph showing Alamar Blue fluorescent readings on culture Days 1, 3, 7, and 10 for cells either cultured in CMHA/Gelin/GSSG (GSSG) or HyStem-C hydrogels in 3D or on tissue culture plastic (TCP)
Figure 3:
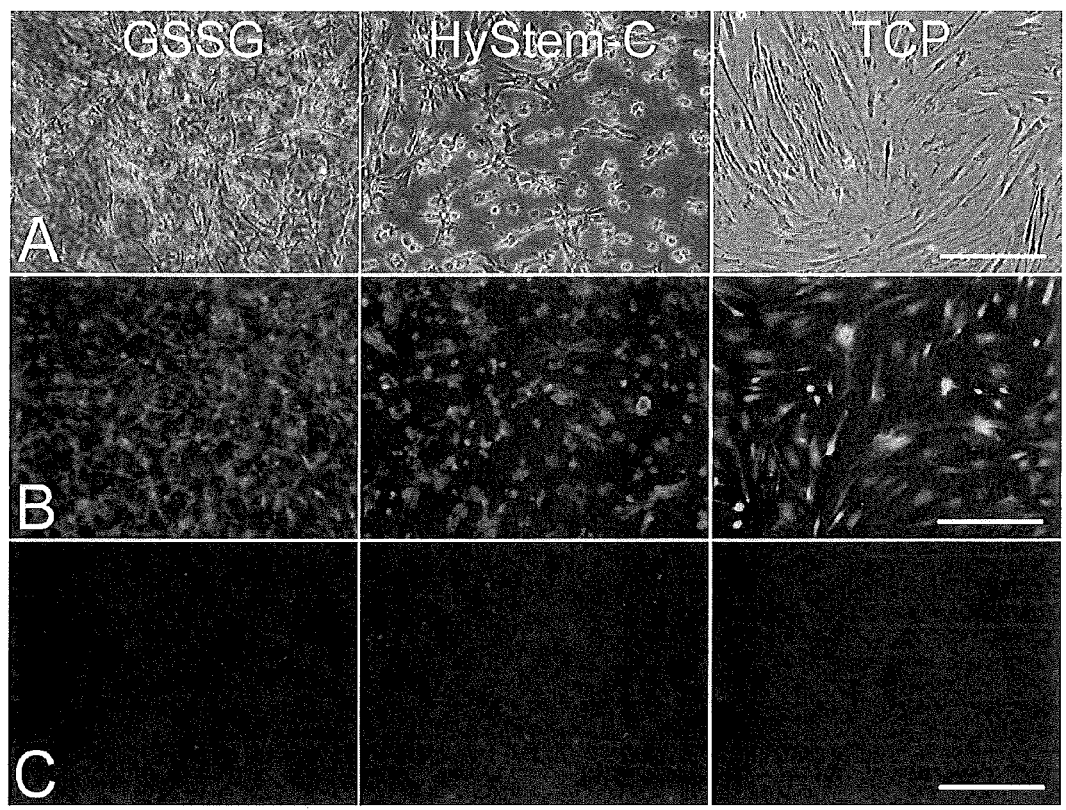
FIG. 3 are photo-micrographs showing images of adipose-derived stem cells encapsulated and cultured (10 days) in different hydrogels (CMHA/Gelin/GSSG (GSSG) or HyStem-C) or on tissue culture plastic (TCP). Phase contrast images (A), calcein AM fluorescence of live cells (B), and propidium iodide fluorescence of dead cells (C). (200 micron scale bar).

There is a growing interest in using adipose derived stem cells (ADSCs) in treating corneal defects, especially in cases of severe ocular surface disease and injuries that result in limbal stem cell depletion and chronic corneal defects [5, 51, 52]. We tested the cytocompatibility of ADSCs in 3D culture by testing the ability of ADSCs to survive after encapsulation in CMHA/Gelin/GSSG hydrogels. 25 µl pads of ADSCs in hydrogel were prepared and cell viability and proliferation were measured over the course of ten days (FIGS. 2, 3). ADSCs were encapsulated either in CMHA/Gelin/GSSG hydrogels or in HyStem-C hydrogels (BioTime, Inc. Alameda, Calif.) as well as plated on tissue culture plastic for comparison. All proliferation rates were standardized to those from CMHA/Gelin/GSSG hydrogels. While increasing proliferation was observed from 1-10 days for all matrices, ADSCs proliferated significantly faster in CMHA/Gelin/GSSG hydrogels than in HyStem-C gels (FIG. 2). Cell morphology and viability was also tested at day 10 using bright field and fluorescent imaging after live-dead staining (FIG. 3). Two major morphological cell shapes were observed: stretched, spindle-like shaped cells and single rounded cells (FIG. 3). The cells in the CMHA/Gelin/GSSG hydrogels had a mixture of spindle-like shaped and rounded cells compared to mostly rounded cells in HyStem-C (FIG. 3). These differences may be in part due to the difference in matrix stiffness since the HyStem-C gel is approximately three times stiffer than the CMHA/Gelin/GSSG gels [34, 53]. Proliferation of ADSC on tissue culture plastic was nearly as fast as that in the CMHA/Gelin/GSSG gels (FIG. 2). Its cells were stretched and spindle shaped due to the absence of matrix impeding their cell elongation and migration [53, 54] (FIG. 3).

Example 7: Covalent Linking of Peptides

After N-terminal maleimido-tagged peptides (Anaspec, Inc. Fremont, CCA) were resuspended in 1xPBS, 1 volume 10 mM peptide was mixed with nine volumes CMHA-S, and reaction was allowed to occur at room temperature in the dark, overnight. GSSG was added to a final concentration of 4 mM (brings peptide final concentration to 0.88 mM) and the mixture allowed to form gels in a 48-well multiwell plate. Unreacted peptides were removed by three washes of at least five volumes 1xPBS at 75 rpm 37° C., for at least 4 hr each [44]. ADSC or BM-MSC in DMEM/10% FBS were then added to each well (15,000 cells/well in a 48 well plate) and allowed to attach overnight. On the final day, the cells were imaged by fluorescence using calcein AM stain.

Figure 4:
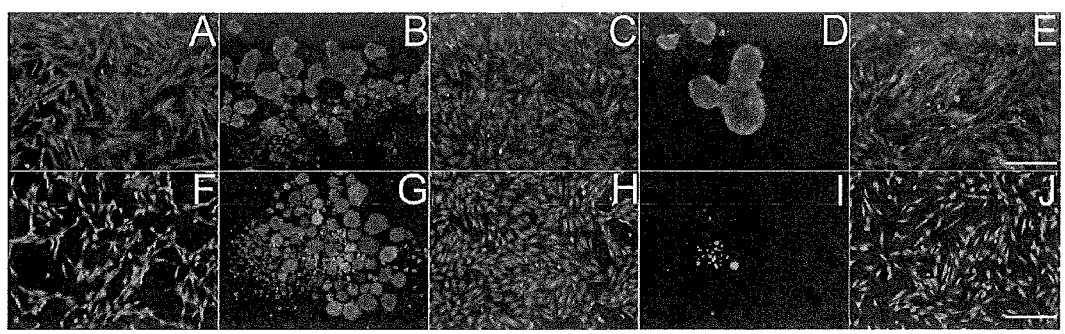
FIG. 4 are photo-micrographs showing fluorescent images of ADSC (A-E) or BM-MSC (F-I) cultured on CMHA/GSSG hydrogels functionalized with peptides. A, F: RGDS peptide; B, G: RDGS peptide; C, H: Gelin-S; D, I: none (i.e. no Gelin-S); E, J: Tissue culture plastic control. (200 micron scale bar).

While the thiol-disulfide exchange reaction permits large thiolated macromolecules like CMHA-S (average MW 240 kDa) and Gelin-S (average MW 20 kDa) to be crosslinked to each other, small thiol-containing peptides such as the peptide CRGDS and cysteine-labeled fluors had poor robustness as measured by cell adhesion studies using adipose-derived stem cells and hydrogel fluorescence measurements (data not shown). As an alternative, maleimido-tagged RGDS (Mal-RGDS) peptide was used to functionalize CMHA-S since maleimides react with free sulfhydryls at neutral pH using the Michael addition reaction [55]. After this reaction, GSSG was added to form the CMHA/GSSG hydrogels. Incorporation of the Mal-RGDS peptide allowed ADSC and BM-MSC cells to attach and spread (FIGS. 4A, 4F). In contrast, the scrambled sequence Mal-RDGS did not allow any ADSC or BM-MSC to attach, causing the cells to round and eventually aggregate at the center of the well (FIGS. 4B, 4G). As controls, both cell types were plated and showed cellular attachment on CMHA/Gelin/GSSG and tissue culture plastic (FIGS. 4C, 4H, 4E, 4J) while showing no attachment on CMHA/GSSG hydrogels (FIGS. 4D, 4I). This data indicates that cellular attachment was due to the coupling of the Mal-RGDS sequence to the CMHA-S and suggests that any variety of small cargo with a maleimido group could be covalently linked to the CMHA-S molecule followed by hydrogel crosslinking with GSSG.

Example 8: In Vivo Biocompatibility Studies

All animal studies were performed at Pacific BioLabs (Hercules, Calif.) and in compliance with all applicable sections of the Final Rules of the Animal Welfare Act Regulations (9 CFR1-3), the Public Health Service Policy on Humane Care and Use of laboratory Animals, the Guide for the Care and Use of Laboratory Animals, and the guidelines of the Pacific BioLabs Institutional Animal Care and Use committee. For intracutaneous studies, New Zealand White adult rabbits (n=4) were used with a weight range of 2.2-3.3 kg each. CMHA/Gelin/GSSG hydrogels (GSSG final concentration: 4 mM) were prepared as described above. After the fur on the back of each animal was shaved and prior to gelation, 0.2 ml was injected intracutaneously using a 22 gauge needle. CMHA/Gelin/GSSG hydrogels were allowed to gel in situ. 0.2 ml Juvederm Ultra XC (Allergan Inc., Irvine, Calif.) was also injected in the same animal as a control comparator. Animals were observed daily for adverse reactions. Animals were then scored for signs of erythema, eschar, and edema irritation according to the ISO 10993-10:2010 (E) biocompatibility test guidelines. Animals were scored daily for the 1st 3 days, at 1st week, and then weekly thereafter. On Day 21 after last scoring, all animals were euthanized per standard operating protocols.

For ophthalmic studies, New Zealand White adult rabbits (n=4) were used with a weight range of 2.2-3.3 kg each. CMHA/GSSG hydrogels (GSSG final concentration: 4 mM) were prepared as described above. Prior to gelation, the upper eyelid of a rabbit was raised and a 0.2 ml subconjunctival perilimbal injection was given superior temporal using a 22 gauge needle. The CMHA/GSSG hydrogel was allowed to gel in situ. After the sample administration, the animals received topical antibiotic and systemic analgesia when necessary. 0.2 ml of Healon Ophthalmic Viscosurgical Device (OVD; Abbott Medical Optics, Santa Ana, Calif.) was injected in the same manner and location in either separate animals or contralateral eyes in the same animal as a control comparator. Animals were observed daily for adverse reactions. Animals were scored daily for the 1st week and weekly thereafter. Animals were scored for signs of discharge, erythema, or irritation according to the Classification system for Grading Ocular Lesions adopted from the ISO 10993-10:20010(E) biocompatibility test. On Day 14 after last scoring, all animals were euthanized per standard operating protocols.

Figure 5:
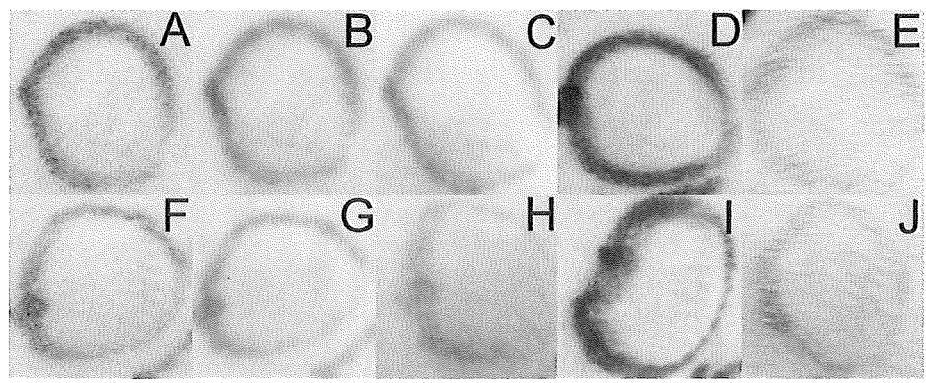
FIG. 5 shows representative photographs of rabbit skin after intracutaneous hydrogel injection over two weeks. CMHA/Gelin/GSSG gels (A-E) and Juvederm (F-J) are shown. The post injection time points are 24 hrs (A, F); 48 hrs (B, G); 72 hrs (C, H); 7 days (D, I); 14 days (E, J).

Since subcutaneous and subconjunctival delivery of therapeutics is commonplace, the biocompatibility of the GSSG hydrogels was evaluated in the intracutaneous area of the skin and in the subconjunctival space of the eye by injecting a small volume and observing safety, tolerability, and changes in appearance of the test articles in vivo over the course of two weeks. The injections were well tolerated, with minimal to mild clinical and microscopic ocular findings attributable to either the test article and or the controls. During the course of the skin experiment with CMHA/Gelin/GSSG hydrogels, there was a minimal bolus (edema score between 0 and 1), and minimal redness (erythema scores of 1 for the first 72 hrs and scores of 0 thereafter) (FIG. 5). The currently marketed hyaluronate dermal filler, Juvederm Ultra XC, was used as a comparator. Redness scores were comparable between the test article and the Juvederm control (erythema scores of 0 to 1) but the injected Juvederm bolus was more clearly visible with more edema (edema scores between 1 and 2).

Figure 6:
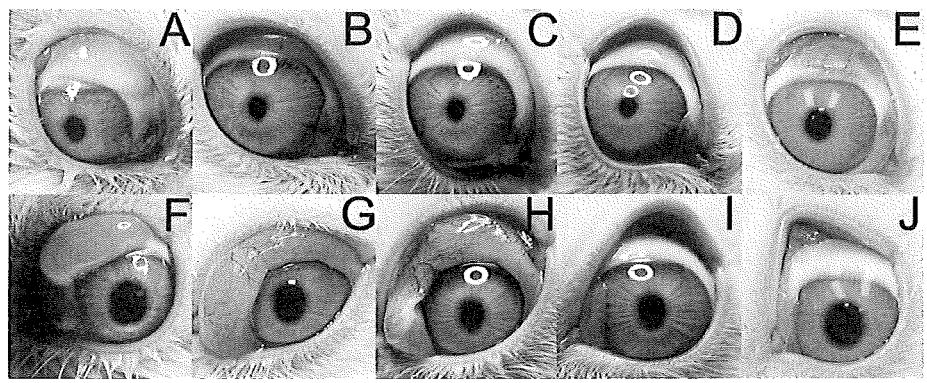
FIG. 6 shows representative photographs of rabbit eye after subconjunctival hydrogel injection over two weeks. CMHA/GSSG gels (A-E) and Healon comparator (F-J) are shown. The post injection time points are 0 hrs (A, F); 24 hrs (B, G); 48 hrs (C, H); 7 days (D, I); 14 days (E, J).

Similarly, during the course of the ocular experiment with CMHA/GSSG hydrogel used as the test article, there was a prominent depot of hydrogel visible subconjunctivally due to the presence of the gel (swelling score of 1) but minimal redness of the conjunctiva and minimal eye discharge (Scores 0 or 1) throughout the course of the study (FIG. 6). The cornea remained clear (Score 0; opacity and percent area affected negligible) (FIG. 6). A currently marketed ophthalmic surgical viscoelastic composed on non-crosslinked high molecular weight hyaluronan, Healon [56], was used as a comparator. The in-life safety and tolerability daily results were comparable, with Healon having scores of 0 and 1 for the same ocular safety parameters (FIG. 6). Close daily inspection of the subconjunctival depot showed that the Healon depot resolved and was resorbed faster than that from CMHA/GSSG (FIG. 6). This result is expected since non-crosslinked hyaluronic acid degrades in hours [57].

Example 9: GM-CSF Elution from Four Hydrogel Formulations

Four HyStem formulations were prepared, each incorporating recombinant human granulocyte/macrophage colony-stimulating factor (GM-CSF, PeproTech Inc., Catalog #300-03) to a final concentration of 0.1 mg/mL. 0.1% BSA and 0.1% EDTA were also incorporated into each hydrogel. The four HyStem formulations were as follows: 1) HyStem (Glycosil 0.8%, Extralink 0.2%); 2) HyStem-Stiff (Glycosil 1.6%, Extralink 0.8%); 3) HyStem-GSSG (Glycosil 0.8%, GSSG 4 mM); and 4) HyStem-HP (Glycosil 0.8%, thiolated Heprin 0.0024%, Extralink 0.2%).

Figure 7:
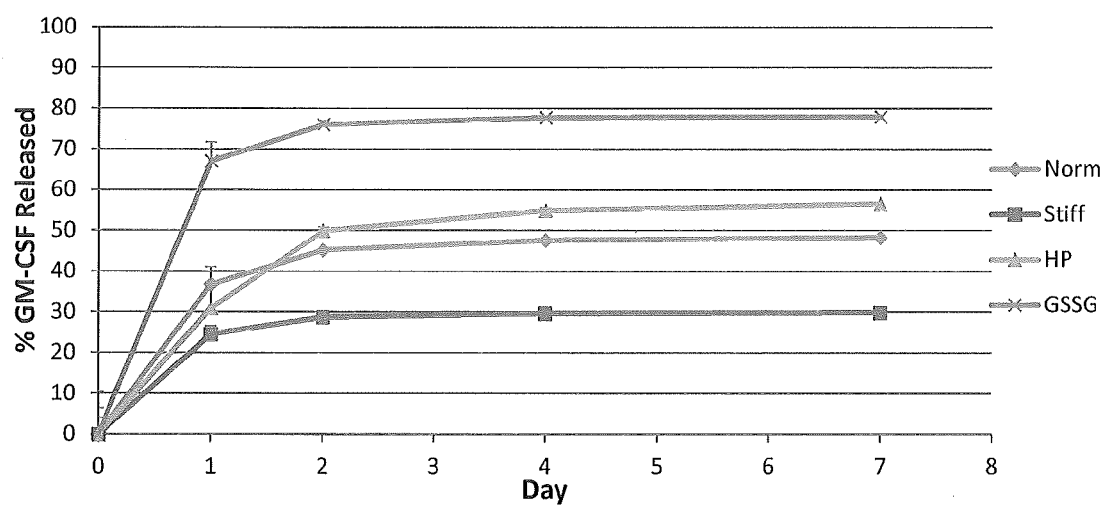
FIG. 7 is a graph showing elution profiles for four different hydrogel formulations (HyStem, HyStem-Stiff, HyStem-GSSG and HyStem-HP) over seven days.

After preparing 125 μl hydrogels in a 48-well plate in triplicate, release solution (1×PBS, 1% BSA, 1 mM EDTA, 10 μg/mL heparin, 1% penicillin/streptomycin) was pipetted over the hydrogels and the hydrogels were shaken at 75 rpm, 37° C. for seven days. Supernatants were withdrawn at each time point (1, 2, 4, 7 days) followed by adding equal volumes of fresh release solution in each hydrogel. ELISA analysis was then performed using commercially available reagents (R&D Systems, catalog #DGM00). In all gel formulations, majority of GM-CSF release occurred by day 4 (FIG. 7). HyStem-GSSG released 78% of GM-CSF contained within the gel by day four, whereas the other three gel formulations released between 30-55% of GM-CSF by day four (FIG. 7).

REFERENCES

[1] Thakur A, Fitzpatrick S, Zaman A, Kugathasan K, Muirhead B, Hortelano G, et al. Strategies for ocular siRNA delivery: Potential and limitations of non-viral nanocarriers. Journal of biological engineering 2012; 6:7.

[2] Kaigler D, Avila G, Wisner-Lynch L, Nevins M L, Nevins M, Rasperini G, et al. Platelet-derived growth factor applications in periodontal and peri-implant bone regeneration. Expert opinion on biological therapy 2011; 11:375-85.

[3] Group C R, Martin D F, Maguire M G, Ying G S, Grunwald J E, Fine S L, et al. Ranibizumab and bevacizumab for neovascular age-related macular degeneration. The New England journal of medicine 2011; 364:1897-908.

[4] Gaudana R, Jwala J, Boddu S H, Mitra A K. Recent perspectives in ocular drug delivery. Pharmaceutical research 2009; 26:1197-216.

[5] Espandar L, Bunnell B, Wang G Y, Gregory P, McBride C, Moshirfar M. Adipose-derived stem cells on hyaluronic acid-derived scaffold: a new horizon in bio-engineered cornea. Archives of ophthalmology 2012; 130:202-8.

[6] Ballios B G, Cooke M J, van der Kooy D, Shoichet M S. A hydrogel-based stem cell delivery system to treat retinal degenerative diseases. Biomaterials 2010; 31:2555-64.

[7] Liu Y, Wang R, Zarembinski T I, Doty N, Jiang C, Regatieri C, et al. The application of hyaluronic Acid hydrogels to retinal progenitor cell transplantation. Tissue engineering Part A 2013; 19:135-42.

[8] Carr A J, Vugler A A, Hikita S T, Lawrence J M, Gias C, Chen L L, et al. Protective effects of human iPS-derived retinal pigment epithelium cell transplantation in the retinal dystrophic rat. PloS one 2009; 4:e8152.

[9] Molokhia S A, Thomas S C, Garff K J, Mandell K J, Wirostko B M. Anterior eye segment drug delivery systems: current treatments and future challenges. Journal of ocular pharmacology and therapeutics: the official journal of the Association for Ocular Pharmacology and Therapeutics 2013; 29:92-105.

[10] Giano M C, Pochan D J, Schneider J P. Controlled biodegradation of self-assembling beta-hairpin peptide hydrogels by proteolysis with matrix metalloproteinase-13. Biomaterials 2011; 32:6471-7.

[11] Mooney D J, Vandenburgh H. Cell delivery mechanisms for tissue repair. Cell stem cell 2008; 2:205-13.

[12] Terrovitis J V, Smith R R, Marban E. Assessment and optimization of cell engraftment after transplantation into the heart. Circulation research 2010; 106:479-94.

[13] Marchini G, Pedrotti E, Pedrotti M, Barbaro V, Di Iorio E, Ferrari S, et al. Long-term effectiveness of autologous cultured limbal stem cell grafts in patients with limbal

[14] Tucker B A, Park I H, Qi S D, Klassen H J, Jiang C, Yao J, et al. Transplantation of adult mouse iPS cell-derived photoreceptor precursors restores retinal structure and function in degenerative mice. PloS one 2011; 6:e18992.

[15] Cai S, Liu Y, Zheng Shu X, Prestwich G D. Injectable glycosaminoglycan hydrogels for controlled release of human basic fibroblast growth factor. Biomaterials 2005; 26:6054-67.

[16] Zhang W, Wang X, Wang S, Zhao J, Xu L, Zhu C, et al. The use of injectable sonication-induced silk hydrogel for VEGF(165) and BMP-2 delivery for elevation of the maxillary sinus floor. Biomaterials 2011; 32:9415-24.

[17] Overman J J, Clarkson A N, Wanner I B, Overman W T, Eckstein I, Maguire J L, et al. A role for ephrin-A5 in axonal sprouting, recovery, and activity-dependent plasticity after stroke. Proceedings of the National Academy of Sciences of the United States of America 2012; 109: E2230-9.

[18] Garbern J C, Minami E, Stayton P S, Murry C E. Delivery of basic fibroblast growth factor with a pH-responsive, injectable hydrogel to improve angiogenesis in infarcted myocardium. Biomaterials 2011; 32:2407-16.

[19] Koutsopoulos S, Unsworth L D, Nagai Y, Zhang S. Controlled release of functional proteins through designer self-assembling peptide nanofiber hydrogel scaffold. Proceedings of the National Academy of Sciences of the United States of America 2009; 106:4623-8.

[20] Laflamme M A, Chen K Y, Naumova A V, Muskheli V, Fugate J A, Dupras S K, et al. Cardiomyocytes derived from human embryonic stem cells in pro-survival factors enhance function of infarcted rat hearts. Nature biotechnology 2007; 25:1015-24.

[21] Zhong J, Chan A, Morad L, Kornblum H I, Fan G, Carmichael S T. Hydrogel matrix to support stem cell survival after brain transplantation in stroke. Neurorehabilitation and neural repair 2010; 24:636-44.

[22] Compte M, Cuesta A M, Sanchez-Martin D, Alonso-Camino V, Vicario J L, Sanz L, et al. Tumor immunotherapy using gene-modified human mesenchymal stem cells loaded into synthetic extracellular matrix scaffolds. Stem cells 2009; 27:753-60.

[23] Kompella U B, Kadam R S, Lee V H. Recent advances in ophthalmic drug delivery. Therapeutic delivery 2010; 1:435-56.

[24] Caicco M J, Zahir T, Mothe A J, Ballios B G, Kihm A J, Tator C H, et al. Characterization of hyaluronan-methylcellulose hydrogels for cell delivery to the injured spinal cord. Journal of biomedical materials research Part A 2012.

[25] Yang G, Espandar L, Mamalis N, Prestwich G D. A cross-linked hyaluronan gel accelerates healing of corneal epithelial abrasion and alkali burn injuries in rabbits. Veterinary ophthalmology 2010; 13:144-50.

[26] Mazumder M A, Fitzpatrick S D, Muirhead B, Sheardown H. Cell-adhesive thermogelling PNIPAAm/hyaluronic acid cell delivery hydrogels for potential application as minimally invasive retinal therapeutics. Journal of biomedical materials research Part A 2012; 100:1877-87.

[27] Shu X Z, Ghosh K, Liu Y, Palumbo F S, Luo Y, Clark R A, et al. Attachment and spreading of fibroblasts on an RGD peptide-modified injectable hyaluronan hydrogel. Journal of biomedical materials research Part A 2004; 68:365-75.

[28] Fairbanks B D, Schwartz M P, Halevi A E, Nuttleman C R, Bowman C N, Anseth K S. A versatile synthetic exracellular marix mimic via thiol-norbornene photopolymerization. Advanced materials 2009; 21:5005-10.

[29] Diabetic Retinopathy Clinical Research N, Writing C, Aiello L P, Beck R W, Bressler N M, Browning D J, et al. Rationale for the diabetic retinopathy clinical research network treatment protocol for center-involved diabetic macular edema. Ophthalmology 2011; 118:e5-14.

[30] Shu X Z, Liu Y, Luo Y, Roberts M C, Prestwich G D. Disulfide cross-linked hyaluronan hydrogels. Biomacromolecules 2002; 3:1304-11.

[31] Zheng Shu X, Liu Y, Palumbo F S, Luo Y, Prestwich G D. In situ crosslinkable hyaluronan hydrogels for tissue engineering. Biomaterials 2004; 25:1339-48.

[32] Prestwich G D. Hyaluronic acid-based clinical biomaterials derived for cell and molecule delivery in regenerative medicine. Journal of controlled release: official journal of the Controlled Release Society 2011; 155:193-9.

[33] Prestwich G D, Erickson I E, Zarembinski T I, West M, Tew W P. The translational imperative: making cell therapy simple and effective. Acta biomaterialia 2012; 8:4200-7.

[34] Vanderhooft J L, Alcoutlabi M, Magda J J, Prestwich G D. Rheological properties of cross-linked hyaluronan-gelatin hydrogels for tissue engineering. Macromolecular bioscience 2009; 9:20-8.

[35] Hanjaya-Putra D, Yee J, Ceci D, Truitt R, Yee D, Gerecht S. Vascular endothelial growth factor and substrate mechanics regulate in vitro tubulogenesis of endothelial progenitor cells. Journal of cellular and molecular medicine 2010; 14:2436-47.

[36] Rieke E R, Amaral J, Becerra S P, Lutz R J. Sustained subconjunctival protein delivery using a thermosetting gel delivery system. Journal of ocular pharmacology and therapeutics: the official journal of the Association for Ocular Pharmacology and Therapeutics 2010; 26:55-64.

[37] Gallogly M M, Starke D W, Mieyal J J. Mechanistic and kinetic details of catalysis of thiol-disulfide exchange by glutaredoxins and potential mechanisms of regulation. Antioxidants & redox signaling 2009; 11:1059-81.

[38] Forman H J, Zhang H, Rinna A. Glutathione: overview of its protective roles, measurement, and biosynthesis. Molecular aspects of medicine 2009; 30:1-12.

[39] Meister A. Glutathione metabolism and its selective modification. The Journal of biological chemistry 1988; 263:17205-8.

[40] Townsend D M, Pazoles C J, Tew K D. NOV-002, a mimetic of glutathione disulfide. Expert opinion on investigational drugs 2008; 17:1075-83.

[41] Sreekumar P G, Spee C, Ryan S J, Cole S P, Kannan R, Hinton D R. Mechanism of RPE cell death in alpha-crystallin deficient mice: a novel and critical role for MRP1-mediated GSH efflux. PloS one 2012; 7:e33420.

[42] Ballatori N, Krance S M, Notenboom S, Shi S, Tieu K, Hammond C L. Glutathione dysregulation and the etiology and progression of human diseases. Biological chemistry 2009; 390:191-214.

[43] Zuk P A, Zhu M, Mizuno H, Huang J, Futrell J W, Katz A J, et al. Multilineage cells from human adipose tissue: implications for cell-based therapies. Tissue engineering 2001; 7:211-28.

[44] Ananthanarayanan B, Kim Y, Kumar S. Elucidating the mechanobiology of malignant brain tumors using a brain matrix-mimetic hyaluronic acid hydrogel platform. Biomaterials 2011; 32:7913-23.

[45] Wu C, Belenda C, Leroux J C, Gauthier M A. Interplay of chemical microenvironment and redox environment on thiol-disulfide exchange kinetics. Chemistry 2011; 17:10064-70.

[46] Engler A J, Sen S, Sweeney H L, Discher D E. Matrix elasticity directs stem cell lineage specification. Cell 2006; 126:677-89.

[47] Klein E A, Yin L, Kothapalli D, Castagnino P; Byfield F J, Xu T, et al. Cell-cycle control by physiological matrix elasticity and in vivo tissue stiffening. Current biology: CB 2009; 19:1511-8.

[48] Liang Y, Jensen T W, Roy E J, Cha C, Devolder R J, Kohman R E, et al. Tuning the non-equilibrium state of a drug-encapsulated poly(ethylene glycol) hydrogel for stem and progenitor cell mobilization. Biomaterials 2011; 32:2004-12.

[49] Cooper A J, Pinto J T, Callery P S. Reversible and irreversible protein glutathionylation: biological and clinical aspects. Expert opinion on drug metabolism & toxicology 2011; 7:891-910.

[50] Zustiak S P, Leach J B. Characterization of protein release from hydrolytically degradable poly(ethylene glycol) hydrogels. Biotechnology and bioengineering 2011; 108:197-206.

[51] Martinez-Conesa E M, Espel E, Reina M, Casaroli-Marano R P. Characterization of ocular surface epithelial and progenitor cell markers in human adipose stromal cells derived from lipoaspirates. Investigative ophthalmology & visual science 2012; 53:513-20.

[52] Du Y, Roh D S, Funderburgh M L, Mann M M, Marra K G, Rubin J P, et al. Adipose-derived stem cells differentiate to keratocytes in vitro. Molecular vision 2010; 16:2680-9.

[53] Mohand-Kaci F, Assoul N, Martelly I, Allaire E, Zidi M. Optimized Hyaluronic Acid-Hydrogel Design and Culture Conditions for Preservation of Mesenchymal Stem Cell Properties. Tissue engineering Part C, Methods 2012.

[54] Chen X, Thibeault S L. Biocompatibility of a synthetic extracellular matrix on immortalized vocal fold fibroblasts in 3-D culture. Acta biomaterialia 2010; 6:2940-8.

[55] Iha R K, Wooley K L, Nystrom A M, Burke D J, Kade M J, Hawker C J. Applications of orthogonal "click" chemistries in the synthesis of functional soft materials. Chemical reviews 2009; 109:5620-86.

[56] Higashide T, Sugiyama K. Use of viscoelastic substance in ophthalmic surgery—focus on sodium hyaluronate. Clinical ophthalmology 2008; 2:21-30.

[57] Laurent T C, Fraser J R. Hyaluronan. FASEB journal: official publication of the Federation of American Societies for Experimental Biology 1992; 6:2397-404.

[58] Firer M A, Gellerman G. Targeted drug delivery for cancer therapy: the other side of antibodies. Journal of hematology & oncology 2012; 5:70.

[59] Wang J, Lu Z, Wientjes M G, Au J L. Delivery of siRNA therapeutics: barriers and carriers. The AAPS journal 2010; 12:492-503.

[60] Jo N, Mailhos C, Ju M, Cheung E, Bradley J, Nishijima K, et al. Inhibition of platelet-derived growth factor B signaling enhances the efficacy of anti-vascular endothelial growth factor therapy in multiple models of ocular neovascularization. The American journal of pathology 2006; 168:2036-53.

[61] Deveza L, Choi J, Yang F. Therapeutic angiogenesis for treating cardiovascular diseases. Theranostics 2012; 2:801-14.

[62] Burman S, Sangwan V. Cultivated limbal stem cell transplantation for ocular surface reconstruction. Clinical ophthalmology 2008; 2:489-502.

[63] Terrovitis J, Kwok K F, Lautamaki R, Engles J M, Barth A S, Kizana E, et al. Ectopic expression of the sodium-iodide symporter enables imaging of transplanted cardiac stem cells in vivo by single-photon emission computed tomography or positron emission tomography. Journal of the American College of Cardiology 2008; 52:1652-60.

[64] Desai V D, Wang Y, Simirskii V N, Duncan M K. CD44 expression is developmentally regulated in the mouse lens and increases in the lens epithelium after injury. Differentiation; research in biological diversity 2010; 79:111-9.

[65] Keller K E, Sun Y Y, Vranka J A, Hayashi L, Acott T S Inhibition of hyaluronan synthesis reduces versican and fibronectin levels in trabecular meshwork cells. PloS one 2012; 7:e48523.

[66] Contreras-Ruiz L, de la Fuente M, Parraga J E, Lopez-Garcia A, Fernandez I, Seijo B, et al. Intracellular trafficking of hyaluronic acid-chitosan oligomer-based nanoparticles in cultured human ocular surface cells. Molecular vision 2011; 17:279-90.

[67] Janmey P A, Miller R T. Mechanisms of mechanical signaling in development and disease. Journal of cell science 2011; 124:9-18.

[68] Turner R A, Wauthier E, Lozoya O, McClelland R, Bowsher J E, Barbier C, et al. Successful transplantation of human hepatic stem cells with restricted localization to liver using hyaluronan grafts. Hepatology 2013; 57:775-84.

[69] Hall J E. Guyton and Hall Physiology Review. 2nd ed. Philadelphia, Pa.: Elsevier Saunders; 2011.

[70] Peyman G A, Hosseini K. Combination therapies in ophthalmology: implications for intravitreal delivery. Journal of ophthalmic & vision research 2011; 6:36-46.

[71] Jeng B H, Dupps W J, Jr. Autologous serum 50% eyedrops in the treatment of persistent corneal epithelial defects. Cornea 2009; 28:1104-8.

[72] York A W, Huang F, McCormick C L. Rational design of targeted cancer therapeutics through the multiconjugation of folate and cleavable siRNA to RAFT-synthesized (HPMA-s-APMA) copolymers. Biomacromolecules 2010; 11:505-14.

[73] Zisch A H, Lutolf M P, Ehrbar M, Raeber G P, Rizzi S C, Davies N, et al. Cell-demanded release of VEGF from synthetic, biointeractive cell ingrowth matrices for vascularized tissue growth. FASEB journal: official publication of the Federation of American Societies for Experimental Biology 2003; 17:2260-2.

[74] Phelps E A, Landazuri N, Thule P M, Taylor W R, Garcia A J. Bioartificial matrices for therapeutic vascularization. Proceedings of the National Academy of Sciences of the United States of America 2010; 107:3323-8.

[75] Rutar M, Natoli R, Provis J M. Small interfering RNA-mediated suppression of Ccl2 in Muller cells attenuates microglial recruitment and photoreceptor death following retinal degeneration. Journal of Neuroinflammation 2012; 9:221.

[76] Peppas N A, Bures P, Leobandung W, Icgikawa H. Hydrogels in pharmaceutical formulations. European Journal of Pharmaceutics and Biopharmaceutics 2000; 50(1):27-46.

[77] Peppas N A, Hilt J Z, Khademhosseini A, Langer R. Hydrogels in biology and medicine: from molecular principles to bionanotechnology. Advanced Materials 2006; 18(11):1345-1360.

[78] Lee K Y, Mooney D J. Hydrogels in tissue engineering. Chemical Reviews 2001; 101(7):1869-1879.
[79] Vercruysse K P, Marecak D M, Marecek J F, Prestwich G D. Synthesis and in vitro degradation of new polyvalent hydrazide cross-linked hydrogels of hyaluronic acid. Bioconjugate Chemistry 1997; 8(5):686-694.
[80] Prestwich G D, Marecak D M, Marecek J F, Vercruysse K P, Ziebell M R. Controlled chemical modification of hyaluronic acid: synthesis, applications, and biodegradation of hydrazide derivatives. Journal of Controlled Release (1998) 53(1-3):93-103.
[81] Burdick J A, Chung C, Jia X, Randolph M A, Langer R. Controlled degradation and mechanical behavior of photopolymerized hyaluronic acid networks. Biomacromolecules 2005; 6(1):386-391.
[82] Gamini A, Paoletti S, Toffanin R, Micali F, Michielin L, Bevilacqua C. Structural investigations of cross-linked hyaluronan. Biomaterials 2002; 23(4):1161-1167.
[83] U.S. Pat. No. 7,928,069
[84] U.S. Pat. No. 7,981,871

What is claimed is:

1. A method of making a hydrogel, the method comprising: 1) reacting a first thiolated polymer with GSSG; and 2) adding a second thiolated polymer to the reaction, thereby forming a hydrogel comprising the first and second thiolated polymers, wherein GSSG is not crosslinked to a polymer.

2. The method of claim 1, wherein the first thiolated polymer is thiolated carboxymethylated hyaluronan (CMHA-S).

3. The method of claim 1, wherein the second thiolated polymer is thiolated gelatin.

4. The method of claim 1, further comprising adding a therapeutic agent at any step.

5. The method of claim 4, wherein the therapeutic agent is chosen from one or more of the following group: a cell, a small molecule, a biologic, a peptide, a protein, and a nucleic acid.

6. The method of claim 4, wherein the therapeutic agent is chosen from one or more of the following group: an antibiotic, an anti-viral, an anti-cancer drug, a growth factor, a hormone, a cytokine, an anti-inflammatory drug, a lipid, a polysaccharide, a nervous system modulator, a pain reliever, a narcotic and an antibody.

7. The method of claim 5, wherein the cell is chosen from one or more of the following group: a cell of the central nervous system, a cell of the digestive system, a hepatocyte, a pancreatic cell, a retinal pigmented epithelial cell, and an adipose cell.

8. The method of claim 4, wherein the therapeutic agent is added before, during or after the hydrogel polymerizes.

9. The method of claim 1, wherein the first thiolated polymer further comprises a maleimido-tagged peptide.

10. The method of claim 9, wherein the peptide comprises RGD.

11. The method of claim 9, wherein the polymer is CMHA-S.

12. The method of claim 1, wherein the first thiolated polymer or the second thiolated polymer or both are comprised of different monomer units.

13. The method of claim 1, wherein the hydrogel has a gelation time of to about 1 minute to about 60 minutes.

14. The method of claim 1, wherein the hydrogel has a gelation onset of between about 1 minute to about 60 minutes.

15. The method of claim 1, wherein the hydrogel has a shear elastic modulus ranging from about 9 to about 37 Pa.

16. The method of claim 4, wherein the therapeutic agent binds to one or more components of the hydrogel by one or more of a covalent bond, ionic bond, hydrogen bond, and van der Waals forces.

17. The method of claim 2, wherein the concentration of CMHA-S is between about 0.1% to 5% w/v.

18. The method of claim 1, wherein the concentration of GSSG is between about 0.1 mM to 54 mM.

19. The method of claim 1, wherein the first thiolated monomer is thiolated carboxymethylated hyaluronan (CMHA-S) and the second thiolated monomer is thiolated gelatin and wherein the thiolated monomers are mixed at a ratio of between about 1:1 to about 5:1 CHHA-S to thiolated gelatin.

20. The method of claim 2, wherein the hydrogel comprises between about 0.8% to 1.6% CMHA-S and wherein the concentration of GSSG is between about 0.1 mM to 54 mM.

21. The method of claim 2, wherein the hydrogel comprises about 0.8% CMHA-S and wherein the concentration of GSSG is about 4 mM.

22. The method of claim 4, wherein between about 65% and 80% of the therapeutic agent is released from the hydrogel over a period of between about 1 day to about 7 days.

23. A method for treating a subject, the method comprising: administering to the subject a hydrogel comprising: a first and a second thiolated polymer crosslinked with GSSG and a therapeutic agent, wherein GSSG catalyzes a crosslinking reaction among the polymers but is not crosslinked.

24. The method of claim 23, wherein the subject has an ocular, cutaneous or subcutaneous injury or disorder.

25. The method of claim 23, wherein the therapeutic agent is selected from the group consisting of a cell, a small molecule, a biologic, a peptide, a protein, and a nucleic acid.

26. The method of claim 23, wherein the therapeutic agent is chosen from the following group: an antibiotic, an anti-viral, an anti-cancer drug, a lipid, a polysaccharide, a growth factor, a hormone, a cytokine, an anti-inflammatory drug, a nervous system modulator, a pain reliever, a narcotic and an antibody.

27. The method of claim 25, wherein the cell is chosen from the following group: a cell of the central nervous system, a cell of the digestive system, a hepatocyte, a pancreatic cell, a retinal pigmented epithelial cell, and an adipose cell.

28. The method of claim 23, wherein the hydrogel is administered subcutaneously or into the subconjunctiva of the subject.

29. The method of claim 23, wherein the hydrogel crosslinks in situ, after administration to the subject.

30. The method of claim 23, wherein the hydrogel is used to treat corneal epithelial wounds; engineer corneal and retinal tissue; repair retinal tissue; and treat stroke, Parkinson's disease, spinal cord injury, MS, diabetes, liver disease, and heart conditions.

31. The method of claim 23, wherein the therapeutic agent binds to one or more components of the hydrogel by one or more of a covalent bond, ionic bond, hydrogen bond, and van der Waals forces.

* * * * *

UNITED STATES PATENT AND TRADEMARK OFFICE
CERTIFICATE OF CORRECTION

PATENT NO. : 10,137,199 B2  
APPLICATION NO. : 14/275795  
DATED : November 27, 2018  
INVENTOR(S) : Thomas Zarembinski et al.

Page 1 of 1

It is certified that error appears in the above-identified patent and that said Letters Patent is hereby corrected as shown below:

In the Claims

Claim 13 (Column 29, Line 61), replace "time of to about" with --time of about--.

Claim 19 (Column 30, Line 11), replace "monomer" with --polymer--.

Claim 19 (Column 30, Line 12), replace "monomer" with --polymer--.

Claim 19 (Column 30, Line 13), replace "monomers" with --polymers--.

Signed and Sealed this  
Tenth Day of December, 2019

Andrei Iancu  
*Director of the United States Patent and Trademark Office*